(12) United States Patent
Macharia et al.

(10) Patent No.: US 8,571,689 B2
(45) Date of Patent: Oct. 29, 2013

(54) MODEL PREDICTIVE CONTROL OF FERMENTATION IN BIOFUEL PRODUCTION

(75) Inventors: Maina A. Macharia, Round Rock, TX (US); Michael E. Tay, Georgetown, TX (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 1484 days.

(21) Appl. No.: 11/927,899

(22) Filed: Oct. 30, 2007

(65) Prior Publication Data

US 2008/0109100 A1 May 8, 2008

Related U.S. Application Data

(60) Provisional application No. 60/863,759, filed on Oct. 31, 2006.

(51) Int. Cl.
| | |
|---|---|
| C12M 1/38 | (2006.01) |
| G05B 13/04 | (2006.01) |
| C12M 1/36 | (2006.01) |
| C12M 1/34 | (2006.01) |
| C12M 1/00 | (2006.01) |

(52) U.S. Cl.
CPC ............... *C12M 41/48* (2013.01); *C12M 41/12* (2013.01); *C12M 41/44* (2013.01); *C12M 41/46* (2013.01); *C12M 45/09* (2013.01); *G05B 13/04* (2013.01)
USPC ............................... 700/28; 700/299; 703/11

(58) Field of Classification Search
USPC .................... 700/1, 28–55, 266–274; 703/11
See application file for complete search history.

(56) References Cited

U.S. PATENT DOCUMENTS

| | | | | |
|---|---|---|---|---|
| 4,652,451 | A  * | 3/1987 | Leedham et al. | 426/11 |
| 5,036,005 | A | 7/1991 | Tedder | |
| 5,595,905 | A  * | 1/1997 | Bishop et al. | 435/243 |
| 6,535,795 | B1 * | 3/2003 | Schroeder et al. | 700/266 |
| 6,934,931 | B2 | 8/2005 | Plumer et al. | |
| 2001/0049595 | A1 * | 12/2001 | Plumer et al. | 703/22 |
| 2002/0077711 | A1 | 6/2002 | Nixon et al. | |

(Continued)

OTHER PUBLICATIONS

Moriyama, H. & Shimizu, K. On-line optimisation of culture temperature for ethanol fermentation using a genetic algorithm. J. Chem. Technol. Biotechnol. 66, 217-222 (1996).*

(Continued)

*Primary Examiner* — Soren Harward
(74) *Attorney, Agent, or Firm* — Fletcher Yoder P.C.; William R. Walbrun; John M. Miller

(57) ABSTRACT

System and method for managing batch fermentation in biofuel production. An optimizer executes a nonlinear multivariate predictive model of a batch fermentation process in accordance with an end of batch objective specifying a target end of batch biofuel concentration to determine an optimal batch trajectory over a temporal control horizon specifying a biofuel and/or sugar concentration trajectory over the batch fermentation process. A nonlinear control model for the batch fermentation process that includes the temporal control horizon driven by biofuel concentration during the batch fermentation process is executed per the determined optimal batch trajectory using received process information as input, thereby generating model output including target values for manipulated variables for the batch fermentation process, including batch fermentation temperature. The batch fermentation process is controlled per the target values to produce biofuel in accordance with the determined optimal batch trajectory, to substantially optimize the end of batch biofuel yield.

25 Claims, 10 Drawing Sheets

(56) References Cited

U.S. PATENT DOCUMENTS

| | | | |
|---|---|---|---|
| 2003/0040642 A1 | 2/2003 | Goto et al. | |
| 2006/0225350 A1 | 10/2006 | Spallone et al. | |
| 2008/0064022 A1* | 3/2008 | Murthy et al. | 703/11 |
| 2008/0103747 A1 | 5/2008 | Macharia et al. | |
| 2008/0103748 A1 | 5/2008 | Axelrud et al. | |
| 2008/0104003 A1 | 5/2008 | Macharia et al. | |
| 2008/0108048 A1 | 5/2008 | Bartee et al. | |
| 2008/0109200 A1 | 5/2008 | Bartee et al. | |
| 2008/0167852 A1 | 7/2008 | Bartee et al. | |

OTHER PUBLICATIONS

Nanba, A., Nishizawa, Y., Tsuchiya, Y. & Nagai, S. Kinetic analysis for batch ethanol fermentation of *Saccharomyces cerevisiae*. Journal of Fermentation Technology 65, 277-283 (1987).*

Qin, S. J. & Badgwell, T. A. A survey of industrial model predictive control technology. Control Engineering Practice 11, 733-764 (2003).*

Oh, K.-K., Kim, S.-W., Jeong, Y.-S. & Hong, S.-I. Bioconversion of cellulose into ethanol by nonisothermal simultaneous saccharification and fermentation. Applied Biochemistry and Biotechnology 89, 15-30 (2000).*

De Andres-Toro, B., et al., "Evolutionary Optimization of an Industrial Batch Fermentation Process", European Control Conference, 1997, http://www.cds.caltech.edu/conferences/related/ECC97/proceeds/501_750/ECC615.PDF, 6 pages.

De Andres-Toro, B, J.M Giron-Sierra, J.A. Lopez-Orozco, C. Ferandez-Conde, "Application of genetic algorithms and simulations for the optimization of batch fermentation control", Systems, Man, and Cybernetics, 1997. 'Computational Cybernetics and Simulation'., 1997 IEEE International Conference on Oct. 12-15, 1997, vol. 1, pp. 392-397.

Madar, Janos, Janos Abonyi, Balaz Balasko, Ferenc Szeifert, "Interactive Evolutionary Computation for Model Based Optimization of Batch Fermentation", European Control Conference, 1997, 6 pages.

Xiao, Jie, Ze-Kui Zhou, Guang-Xin Zhang, "Ant colony system algorithm for the optimization of beer fermentation control", Journal of Zhejiang University Science, ISSN 1009-3095, 2004, 5(12): pp. 1597-1603.

Chang, Raymond. "Physical Chemistry for the BioSciences; Chapter 10: Enzyme Kinetics", University Science Books, 2005, pp. 363-400.

Lin Yan Shuzo Tanaka, "Ethanol fermentation from biomass resources: current state and prospects", Appl. Microbiol. Biotechnol., 69: 627-642, 2006.

Lee, C.-G., C.H. Kim, S.K. Rhee, "A kinetic model and simulation of starch saccharification and simultaneous ethanol fermentation by amyloglucosidase and *Zymomonas mobilis*", Bioprocess Engineering 7, 1992, 335-341.

"Liquefaction of starch from dry-milled grains", Novozymes, 2004, 5 pages.

De Andres-Toro, B., J.M. Giron-Sierra, P. Fernandez-Blanco, J.A. Lopez-Orozco, E. Besada-Portas, "Multiobjective optimization and multivariable control of the beer fermentation process with the use of evolutionary algorithms", Journal of Zhejiang University Science, ISSN 1009-3095, 2004, 5(4): pp. 378-389.

De Andres-Toro, B., J.M. Giron-Sierra, J.A. Lopez-Orozco, C. Fernandez-Conde, J.M. Peinado, F. Garcia-Ochoa, "A kinetic model for beer production under industrial operational conditions", Mathematics and Computers in Simulation 48, 1998, pp. 65-74.

U.S. Appl. No. 12/052,117, filed Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.
U.S. Appl. No. 12/242,531, filed Sep. 30, 2008, Macharia et al.
U.S. Appl. No. 12/242,568, filed Sep. 30, 2008, Macharia et al.
U.S. Appl. No. 12/242,606, filed Sep. 30, 2008, Macharia et al.
U.S. Appl. No. 12/242,635, filed Sep. 30, 2008, Macharia et al.

* cited by examiner

MODEL PREDICTIVE CONTROL OF FERMENTATION IN BIOFUEL PRODUCTION

PRIORITY DATA

This application claims benefit of priority of U.S. provisional application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee, which is hereby incorporated by reference in its entirety as though fully and completely set forth herein.

FIELD OF THE INVENTION

The present invention generally relates to the field of model predictive control of production processes for biofuel and its co-products. More particularly, the present invention relates to systems and methods for model predictive control of a fermentation process in a biofuel production process.

DESCRIPTION OF THE RELATED ART

History of Biofuel

Biofuel refers to any fuel derived from biomass, i.e., from recently living organisms or their bi-products. Biofuel was used in automobiles from approximately 1876-1908. The Otto Cycle (1876) was the first combustion engine designed to use alcohol and gasoline. Henry Ford's Model T (1908) was designed to use biofuel, gasoline, or any combination of the two fuels. However, high government tariffs on alcohol discouraged the use of biofuel, and gasoline became the predominant fuel choice for automobiles for many decades.

The energy crisis of the 1970s renewed the search for an alternative to fossil fuels. The Energy Tax Act of 1978 (H.R. 5263) provided a 4 cents per gallon exemption from Federal excise taxes to motor fuels blended with biofuel (minimum 10 percent biofuel) and granted a 10% energy investment tax credit for biomass-biofuel conversion equipment (in addition to the 10% investment tax credit available) that encouraged plant building. However, by 1985, only 45% of the 163 existing commercial biofuel plants were operational. This high plant failure rate was partially the result of poor business judgment and inefficient engineering design. In 1988, biofuel was used as an oxygenate in Denver, Colo., which mandated the use of oxygenated fuels during winter use. Oxygenated fuels are fuels that have been infused with oxygen to reduce carbon monoxide emissions and NOx emissions created during the burning of the fuel. The Clean Air Act in the 1990s, motivated an additional increase in the use of biofuel as a pollution control additive.

The US Congress passed the Clean Air Act Amendments of 1990, which mandated the use of "reformulated gasoline" containing oxygenates in high-pollution areas. Starting in 1992, Methyl Tertiary Butyl Ether (MTBE) was added to gasoline in higher concentrations in accordance with the Clean Air Act Amendments. Improvements in air quality in many areas has been attributed to the use of gas reformulated with MBTE. However by 2000, MTBE—(a known carcinogenic agent) was found to have contaminated groundwater systems, mostly through leaks in underground gasoline storage tanks. In 2004, California and New York banned MTBE, generally replacing it with ethanol. Several other states started switching soon afterward. The 2005 Energy Bill required a phase out of MTBE and did not provide legal protection for the oil companies. As a result, the oil companies began to replace MTBE with ethanol (one embodiment of a biofuel), thereby spurring growth in the biofuel industry.

Since 2001, there has been a steady rise in crude oil prices that has increased the price of gasoline above the break-even point of the cost of production of biofuel. This has been very beneficial to Mid-west agricultural regions that have always sought ways to diversify demand for agricultural goods and services. Biofuel plants that had depended on subsidies to be profitable are now transitioning to an economically viable venture for this corn-rich region.

Biofuel Production Plants

An exemplary high-level design of a biofuel production plant or process is shown in FIG. 1, which illustrates how biomass is processed through several stages to produce biofuel and one or more co-products. Biomass is first provided to a milling and cooking process, e.g., milling and cooking units 104, where water 102 (and possibly recycled water RW1 and RW2) is added and the biomass is broken down to increase the surface area to volume ratio. This increase in surface area allows for sufficient interaction of the water and biomass surface area to achieve a solution of fermentable sugars in water. The mixture, a biomass and water slurry, is cooked to promote an increase in the amount of contact between the biomass and water in solution and to increase the separation of carbohydrate biomass from the non-carbohydrate biomass. The output of the milling and cooking units 104 (i.e., the fermentation feed or mash) is then sent to a fermentation process, where one or more fermentation units 106 operate to ferment the biomass/water mash produced by the milling and cooking process.

As FIG. 1 indicates, the fermentation process may require additional water 102 to control the consistency of material to the fermentation units (also referred to herein as a fermenter or a fermentation tank). Biomass is converted by yeast and enzymes into a biofuel and by-products such as carbon dioxide, water and non-fermentable biomass (solids), in the fermentation units 106. The fermentation process is a batch process with multiple fermenters in parallel. The batch start times are staggered as shown in FIG. 2 in order to optimize the size of holding tanks and smooth out the flow of fermentation feed to the fermentation process and the flow of biofuel and stillage as output from the fermentation process. FIG. 3 indicates an exemplary plot of active yeast and ethanol concentrations as a function of batch time for a fermentation batch.

The output from the fermentation units 106 is sent to a distillation process, e.g., one or more distillation units 108, to separate biofuel from water, carbon dioxide, and non-fermentable solids. If the biofuel has to be dehydrated to moisture levels less than 5% by volume, the biofuel can be processed through a processing unit called a molecular sieve or similar processing units (including, for example, additive distillation such as cyclohexane that breaks a water/ethanol azeotrope). The finalized biofuel is then processed to ensure it is denatured and not used for human-consumption.

The distillation units 108 separate the biofuel from water. Water 102 is used in the form of steam for heat and separation, and the condensed water is recycled (RW1) back to the milling and cooking units 104, as shown in FIG. 1. Stillage (non-fermentable solids and yeast residue), the heaviest output of the distillation units, is sent to stillage processing for further development of co-products from the biofuel production process.

Stillage processing units 110 separate additional water from the cake solids and recycle this water (RW2) back to the milling and cooking units 104. There are a number of stillage processing options: stillage can be sold with minimal processing, or further processed by separating moisture from the solids product via one or more centrifuge units. From the centrifuge, the non-fermentable solids may be transported to dryers for further moisture removal. A portion of the stillage liquid (centrate) may be recycled back to the fermentation units 106; however, the bulk of the flow is generally sent to evaporator units, where more liquid is separated form the liquid stream, causing the liquid stream to concentrate into syrup, while solid stillage is sent to a drying process, e.g., using a drying unit or evaporator, to dry the solid stillage to a specified water content. The syrup is then sent to the syrup tank. Syrup in inventory can be processed/utilized with a number of options: it can be sprayed in dryers to achieve a specified color or moisture content; it can be added to the partially dried stillage product, or it can be is sold as a separate liquid product. The evaporator unit may have a water byproduct stream that is recycled back to the front end (RW2), e.g., to the milling and cooking units 104.

Note that an energy center 112 supplies energy to various of the processing units, e.g., the milling and cooking units 104, the distillation 108 and mole-sieve units, and the stillage processing units. The energy center 112 may constitute a thermal oxidizer unit and heat recovery steam generator that destroys volatile organic compounds (VOCs) and provides steam to the evaporators, distillation units 108, cooking system units (e.g., in 104), and dehydration units. The energy center 112 is typically the largest source of heat in a biofuel plant In prior art biofuel plants, properties such as temperature or product quality are controlled with control systems utilizing traditional control schemes such as temperature, pressure, level, and/or flow control schemes, which may include proportional integral derivative (PID), cascade, feed-forward, and/or constraint control schemes, among others.

Systems can be open or closed. An open loop system is a system that responds to an input, but the system is not modified because of the behavior of the output. An open loop system receives process input, and generates process output, with no feedback from output back to input. Open loop systems are only defined by the inputs and the inherent characteristics of the system or process. In the biofuel production process, the system may comprise the entire biofuel processing plant, one process section of the biofuel processing plant, such as the milling and cooking units, or a controller for a variable in a process such as the temperature of the cooking units.

In a closed loop system, the inputs are adjusted to compensate for changes in the output, where, for example, these changes may be a deviation from the desired or targeted measurements. The closed loop system senses the change and provides a feedback signal to the process input. The closed loop system receives process input and generates process output, but where at least a portion of the output is provided back to the input as feedback. Process units in the biofuel system may be closed loop systems if they need to be regulated subject to constraints such as product quality, energy costs, or process unit capacity.

Modern plants apply traditional and advanced controls to regulate complex processes to achieve a specific control objective. Traditional PID controllers and other control systems such as ratio controls, feed-forward controls, and process models may be used to control biofuel production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

Most biofuel production facilities mill or steep corn, other grains, or other biomass (e.g. sugarcane), and mix this milled carbohydrate base with water from a variety of sources and quality.

The operating challenge is to provide a steady quality and concentration of feed to the fermentation units. However, due to variability in feed amount, flow rates, mill rates, steep efficiencies, or biomass (e.g., grain) quality, the fermentation output varies dramatically and the process operates sub-optimally due to this large variability. Fermentation end concentrations of biofuel may vary plus or minus 10% or more.

Plants are currently implemented to provide some information to plant operators to enable them to increase or decrease the feed of fermentable sugar and starch concentrations to fermentation tanks. Plant operators monitor the target feed quality and percent solids in the fermentation feed and run the plants to achieve a target percent solids so that each fermentation batch is started with a rough approximation of the target percent solids and each fermentation process runs over a specific time period in an attempt to achieve an output with approximately the design target percent of biofuel. In addition, a recycle flow rate is typically managed to maintain tank inventory levels within safe operating limits, while providing sufficient water/liquid to mix with grain or other biomass solids to fill a fermentation tank within a targeted time period (i.e. fill a vessel of 180,000 gallons in 15 hours so that the fill rate would be 600 gallons per minute).

In addition, levels of various water sources tend to increase or decrease, and operators or level controllers may adjust flows to regain targeted levels. In general, these applications are controlled with flow, level or mill speed controllers (e.g., regulatory level controllers). Some applications of ratio controllers are used in current control systems (e.g., to monitor the ratio of enzyme flow rates to grain slurry flow rates).

Two additional calculated parameters are also important to plant operators. The first parameter is Percent Recycle (also referred to as backset), which is the fractional percentage of recycled thin stillage (fermentation liquor output from a centrifuge that separates out cattle feed solids). Percent Recycle is managed manually to maintain both a rough thin stillage inventory and to operate within a range of fractional percent backset. It is important to manage the fractional percent backset, because the fermentation liquor contains both residual yeast nutrients along with yeast waste products from previous fermentation. Too little or too much backset can be a problem for fermentation productivity.

The second parameter is Fermentation Inventory, which is a totalized inventory across the filling, draining and fermenting fermentation vessels and key auxiliary equipment. If this total inventory level is held within an acceptably stable band, the front plant section, i.e., the milling/cooking, and fermentation processes, can be managed to match the back plant section, i.e., the distillation and stillage processes, across all batch sequentially operated fermentation vessels. If totalized batch volume is constant, then filling is balanced with draining across multiple parallel batch fermentation vessels.

A biofuel production plant may require numerous adjustments, e.g., on a minute-to-minute basis, in response to changes and shifting constraints if the plant process is to operate in an optimal manner. Due to this complexity, human operators are not capable of actively optimizing a biofuel production process. Consequently, operators generally operate a plant in a less efficient operating mode.

Thus, improved systems and methods for biofuel production are desired.

SUMMARY OF THE INVENTION

Embodiments of a system and method are presented for managing a fermentation process of a biofuel production process.

In one embodiment, a nonlinear multivariate predictive model of a batch fermentation process of a biofuel production process may be provided, where the nonlinear multivariate predictive model is usable to optimize end of batch biofuel yield. Additionally, a nonlinear control model for the batch fermentation process may be provided, where the nonlinear control model includes a temporal control horizon driven by biofuel concentration during the batch fermentation process. In one embodiment, the nonlinear multivariate predictive model may be a function of two or more of: yeast influence, temperature, biomass concentration, enzyme concentration, batch progress, and/or pH, among others. Note that the yeast influence may include yeast concentration, yeast addition, and/or yeast activity. The nonlinear multivariate predictive model may receive an end of batch objective specifying a target end of batch biofuel concentration.

An optimizer may execute the nonlinear multivariate predictive model to determine an optimal batch trajectory over the temporal control horizon in accordance with the end of batch objective. The optimal batch trajectory may specify a biofuel concentration and/or sugar concentration trajectory over the batch fermentation process. The optimal batch trajectory may then be provided to the nonlinear control model as a control objective.

Process information for the batch fermentation process may be received, and the nonlinear control model executed in accordance with the determined optimal batch trajectory using the received process information as input, thereby generating model output comprising target values for a plurality of manipulated variables for the batch fermentation process. The plurality of manipulated variables include batch fermentation temperature, i.e., the target values include a target batch fermentation temperature.

The batch fermentation process may then be controlled in accordance with the target values to produce biofuel in accordance with the determined optimal batch trajectory, to substantially optimize the end of batch biofuel yield.

In some embodiments, the method may further include receiving at least one constraint, including one or more of: a constraint on sugar concentration over the batch fermentation process, or a constraint on end of batch sugar concentration. In various embodiments, the optimal batch trajectory over the temporal control horizon, and/or the target values for the plurality of manipulated variables, may be determined subject to the at least one constraint.

The above receiving process information, executing the nonlinear control model, and controlling may be repeated in an iterative manner to achieve targeted biofuel production over a fermentation batch. In one embodiment, the repeating the executing the nonlinear control model may generate target values including or forming a fermentation temperature staging profile for the fermentation batch. In other words, each iteration may generate one or more target values, where the target values generated over a plurality of iterations may compose or comprise a fermentation temperature staging profile for the fermentation batch.

Thus, various embodiments of the present invention may provide for improved control of biofuel batch fermentation, with a resulting improvement in biofuel yields.

BRIEF DESCRIPTION OF THE DRAWINGS

A better understanding of the present invention can be obtained when the following detailed description of the preferred embodiment is considered in conjunction with the following drawings, in which.

Figure 1:
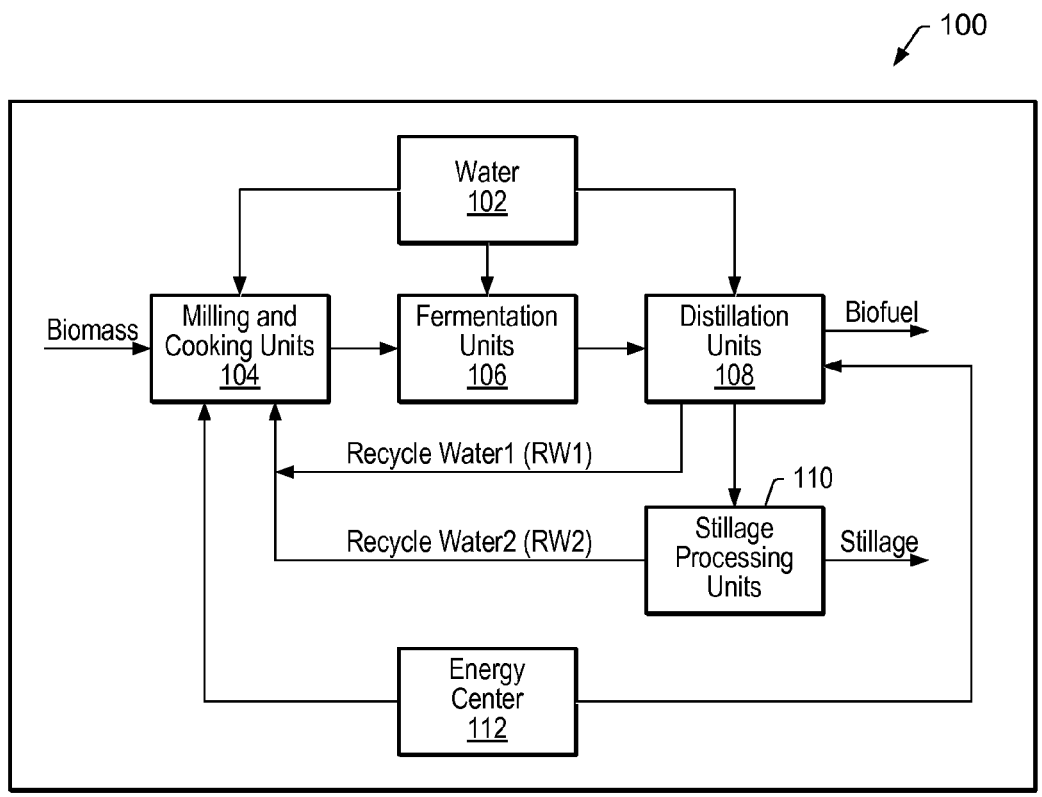
FIG. 1 illustrates one example of a biofuel processing plant, according to the prior art.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Definitions—Biofuel Production Processes

Biofuel—any fuel (or fuels) derived from biomass, i.e., from recently living organisms or their bi-products.

Biofuel production process—a fermentation process surrounded by auxiliary processing units to produce biofuel, other fermentable alcohols for fuel, and high-capacity food grade or chemical grade alcohols.

Biofuel production—a measure of biofuel production within or at the end of a production process. May include measurements such as concentration (e.g., wt. %, volume % or wt./vol. %), volume (e.g., current gallons biofuel within a fermenter) or mass (e.g., current kg biofuel within a fermenter).

Batch processing—a staged discontinuous processing step that includes a start and an end, in contrast to continuous processing that continues without stop, e.g., during a normal operating day or week. Continuous processing is generally represented by fairly steady targets or operations, where at least some parameters change throughout batch processing. For example, biofuel production, e.g., fermentation, starts at low levels at the start of a batch and increases throughout the batch with or without a drop at the end representing degradation rates being higher than production rates. Similarly, yeast cellular concentrations, start at fairly low levels, and generally grow throughout a batch, although they generally have a lag (relatively constant concentrations), exponential growth, stable growth, and degradation phase within a batch.

Slurry—a fermentation feed mash comprising a two-phase (liquid and solid) slurry that will be fermented.

Solids or % solids—fraction or percent of solids in the fermentation feed.

Milling and Cooking Process—continuous processing for pre-fermentation of the fermentation feed, which generally includes grain or cane milling, cooking, mixing with water and processing chemicals, cooking for sterilization and increasing water concentration within solids, and other pre-fermentation processing.

Biomass concentration—content attribute of the fermentation feed specified by one or more of: slurry solids, liquefaction solids, slurry density, liquefaction density, slurry % or fraction carbohydrates, and slurry % or fraction fermentable sugar.

Liquids inventory information—includes water flows, recycle liquid flows, evaporator condensate recycle flow, thin stillage or centrifuge liquor recycle flows, water addition flows, processed water addition flows, slurry flows, mash flows, and various levels or weights for various tanks used to hold inventories of these flows or for intermediate receptacles (e.g. methanator feed tank, slurry feed tank, liquefaction tank, distillate tank, grain silo inventories or other biomass inventories (not water), etc.).

Liquefaction—for grains with high starch content, the starch is liquefied to reduce its carbohydrate chain length and viscosity by adding enzymes or other biologic agents.

Thermal Oxidizer/Heat Recovery Steam Generator (HRSG)—process equipment that is used to destroy volatile organic compounds (VOCs), to reduce air and remove stenches from stillage dryer or evaporation systems. The heat recovery steam generator is used to recover the heat required to destroy the VOCs, and is typically the energy center of the biofuel production process.

Dried Distillers Grains (DDG)—post fermentation solid residue that includes undigested grain residue, other solid residues (enzymes, salts), and yeasts (or other cellular residue) that may be dried and released as a production by-product (generally as animal feed). DDG may also be used herein to include WDG (wet distillers grains), which are only partially dried for local consumption (e.g. without long-term biological stability) and DDGS/WDGS (dried distillers grains with solubles and wet distillers grains with solubles). Solubles includes residue solids that are soluble in water and therefore present in stillage concentrate. Solubles may be partially concentrated (generally with evaporation), and added to DDG or WDG to increase yields and manage by-product inventories.

Enzyme—highly selective biological-based catalyst added to manage specific reactions within a fermentation process. The most common enzymes used today include alpha amylase to rapidly break starches into dextrins, gluco-amylase to break dextrins into glucose, and proteases to break grain proteins into digestible proteins to support cell growth. In the same way as described below, modeling and controlling starch-based fermentations, enzymes specific for cellulosic conversion into biofuel or other enzymes affecting yeast (see below), growth or nutrient availability may be managed.

Yeast—a biofuel producing organism. Yeasts are currently the most commonly used organism in ethanol production although other biofuel producing organisms including genetically engineered *E. coli* can be substituted throughout as the technology described may not be specific to yeast, and may apply to many organisms used in fermentation processes to produce biofuel.

Active Yeast—refers to yeast as defined above that are actively consuming carbohydrates to produce biofuel. Unless otherwise specified, yeast as referred to in this document is by definition active yeast.

Stillage/Whole Stillage—non-fermentable solids and water liquid removed from the bottom of the primary distillation units.

Thin Stillage—the separated liquid from the stillage non-fermentable solids.

Backset—thin stillage that is recycled back to the fermentation feed line and thus introduced into the fermentation process.

Syrup—concentrated thin-stillage with a large portion of the moisture removed. The % solids in syrup are usually in the range of 20-45% solids, but percentages outside this range may occur.

Fermentation Gap—the cumulative sum of all fermentation tanks as well as the beer well. Represented as volume, % volume, level, % level or like designations.

Beer Well—repository of fermentation tank effluent. Holding tank between the fermentation section and distillation section of many biofuel processes, Azeotrope—a special mixture of two compounds, that when in equilibrium, the vapor phase and liquid phase have exactly the same compositions. This makes it difficult to separate the two components to achieve a better purity. Special separation processes are required to break the azeotrop. They comprise azeotropic distillation (add a $3^{rd}$ compound to break the azeotrop), extractive distillation (use a solvent to separate the 2 compounds), or molecular sieve technology (preferentially trap molecules of one component in a molecular sieve bed as the other component passes over the molecular sieve bed).

Volatile Organic Compounds (VOCS)—Organic compounds that tend to vaporize when subject to atmospheric pressure and ambient temperature ranges.

Capacity—capacity is the established maximum production rate of the process, sub-process, or unit under best operating conditions (no abnormal constraints). Capacity is generally a constant within the present capital investment. For new units it is the vendor's specified capacity. For established units, capacity is established by demonstrated historical production rates.

Model—an input/output representation, which represents the relationships between changes in various model inputs and how the model inputs affect each of the model outputs.

Control Model—an input/output representation of a system or process that determines how much an output changes when an input is changed, and may include instantaneous (steady-state) models as well as dynamic models, as defined above. Control models may be univariate (single input effect a single output) or multivariate (multiple inputs effecting multiple outputs).

Dynamic Predictive Model—an input/output representation of a system or process that not only reflects how much an output changes when an input is changed, but with what velocity and over what time-dependent curve an output will change based on one or more input variable changes. A dynamic multivariate predictive model is a dynamic predictive model that represents or encodes relationships among multiple parameters, and is operable to receive multiple inputs, and generate multiple outputs.

Model Predictive Control (or MPC)— use of multivariate dynamic process models to relate controller objectives (targeted controller outputs and constraints) with regulatory controllers (existing single-input/single-output controllers such as ratio flow, temperature, level, speed, or pressure controllers) over a predicted time interval (e.g., 1 minute, 30 minutes, 2 hours, 100 hours, etc.).

Objective Function—encodes an objective that sets the goal or goals for the overall operation of the process, sub-process, or unit. The objective function provides one or more consistent numerical metric(s) to which the process, sub-process, or unit strives to achieve and over which the performance of the process, sub-process, or unit may be measured, e.g., from a business.

Control Variables—(also called controlled variables) those variables that the controller/optimizer tries to bring to a specified value, e.g., to a target value, maximum, etc. The range of allowed values for each control variable may be limited by constraints.

Integrated Variables—integrated control variables are variables that are not stable, but integrate generally with a stable first derivative as a function of time. The most common integrated variable is a tank level where as long as inputs and outputs are imbalanced the level will increase or decrease. Thus, when balanced a change in an input or output flow will cause a tank to either overfill or drain as integrated over time. A controller must use these integration calculations to determine when and how rapidly input or output flows must be adjusted.

Manipulated Variables—those variables over which the management of the process or unit has authority and control, e.g., via regulation of the process with online controllers, and which are changed or manipulated by the controller/optimizer to achieve the targets or goals of the control variables. Manipulated variables may operate within some range of controllable or fixed constraints. Manage is an alternate term for process control.

Disturbance Variable—a variable representing an external influence on a process that, in addition to objective variables and regulatory controllers, is outside the controller scope, and so it acts on the objective variables, but independently of the described controller. Disturbance variables are used in feed-forward disturbance rejection. Disturbance variables are also measured or unmeasured variables over which the management of the process or unit does not have direct authority or control. For example, temperature, humidity, upstream flow, or quality, may all be referred to as measured disturbance variables.

Set Point (targets)—also "setpoint"; the target signal or value for a manipulated variable or targeted controlled variable.

Constraints—Constraints represent limitations on particular operating variables or conditions that affect the achievable production rate of a production unit. Constraints are of two types: controllable and external, defined below. Constraints may include, but are not limited to: safety constraints, equipment constraints, equipment availability constraints, personnel constraints, business execution constraints, control constraints, supply chain constraints, environmental permit and legal constraints. Safety constraints ensure the safety of equipment and personnel. Equipment constraints, such as the maximum open position of a control valve, maximum tank capacity, etc., may limit the physical throughput of the unit. Equipment availability constraints may include, but are not limited to: readiness due to maintenance planning and scheduling, or due to unexpected equipment outages, authorized production level set by the supply chain and production scheduling systems. Personnel constraints refer to limitations on the availability of staffing and support functions, business rules and constraints imposed by contract and policy. Business execution constraints are limits imposed by the time required to execute associated business and contractual tasks and obligations. Control constraints are limits on the maximal position and rate of change of manipulated variables. Supply chain constraints are limits on the availability of raw materials, energy, and production supplies. Environmental permit and legal constraints are limits on air emissions, wastewater, waste disposal systems, and/or environmental constraints imposed upon the performance of the unit, such as river levels and current weather imposed limitations.

Controllable Constraints—constraints imposed on the performance of a process or unit over which the management of the process or unit does have authority and discretionary control. For example, the separation in a distillation tower may be affected by distillation tray fouling. The tray fouling is a function of how the feedstock is processed, and how often the unit is taken offline for cleanup. It is management's discretion as to when the unit is serviced. Controllable constraints change a unit's throughput capacity.

External Constraints—limitations imposed on the performance of the process, sub-process, or unit over which the management of the process, sub-process, or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

System—a system may be defined by the inputs and the characteristics of the system or process. In the biofuel production process, the system may be defined for: the entire biofuel production process, a sub-process of the biofuel production process such as the milling and cooking process, or control of a variable in a sub-process such as the cooking temperature.

Figure 2:
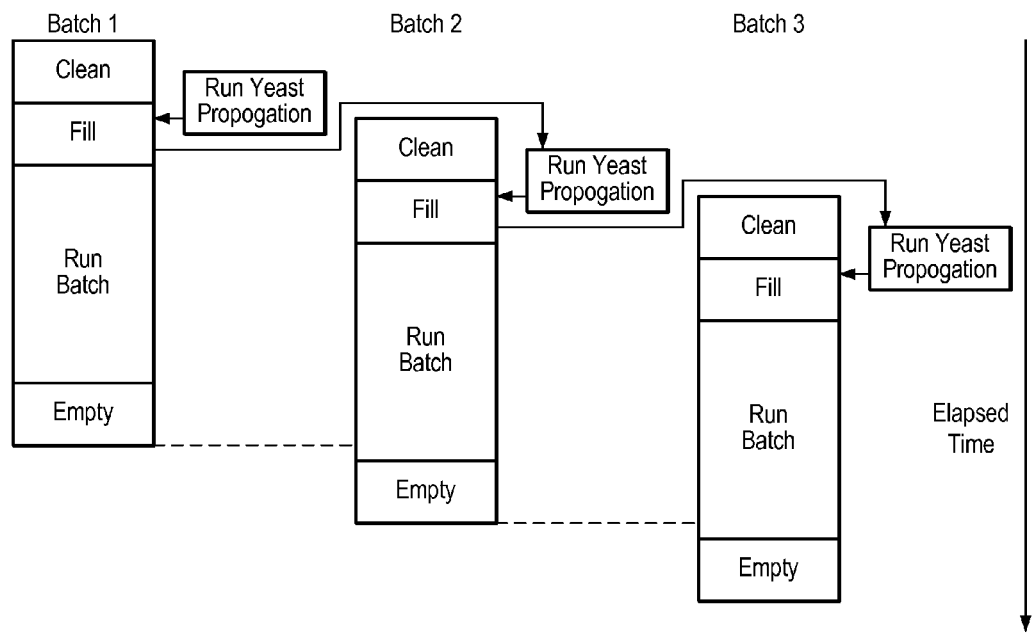
FIG. 2 illustrates a simplified processing flow schematic of three parallel batch fermentation processes with staggered start times, according to the prior art.
Figure 3:
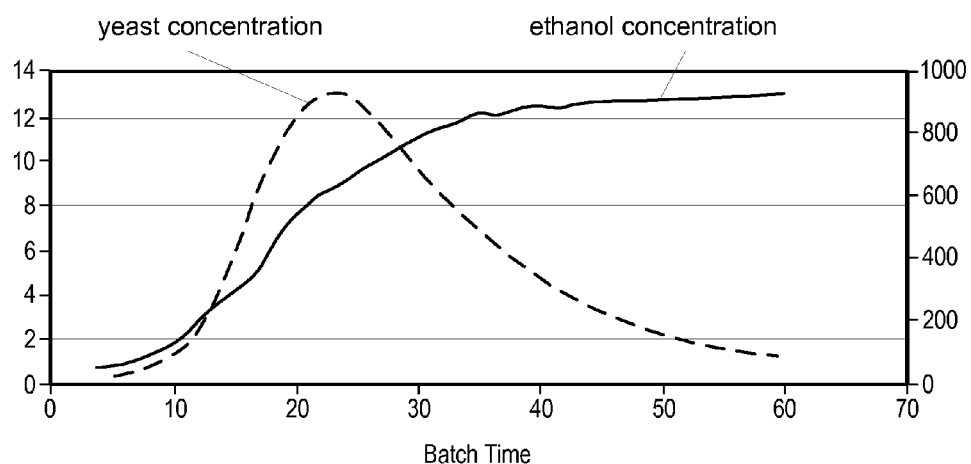
FIG. 3 illustrates an exemplary plot of active yeast and ethanol concentrations as a function of batch time, according to the prior art.

Open Loop Systems—are systems that respond to an input, but the system is not modified because of the behavior of the output (see FIG. 2). For example, in a biofuel system, a reciprocating pump will operate and move at a fixed volume of syrup independent of the upstream and downstream pressure if the reciprocating pump does not have a pressure control system.

Closed Loop Systems—system inputs may be adjusted to compensate for changes in the output. These changes may be a deviation from an objective for the system, impacts of constraints on the system or system variables, or measurements of output variables. The closed loop system may be used to sense the change and feedback the signal to the process input. In biofuel systems, closed loop systems may predominate, since these systems may be regulated subject to constraints such as production (product) quality, energy costs, process unit capacity, etc.

Control System—the regulatory level mechanism by which the manipulated variables are driven to the set points.

Response—the measurement of the current position of the manipulated variable. The response is the feedback of the movement of the manipulated variable to the set point in response to the actions of the control system in its effort to achieve the set point.

Target Profile or Trajectory—a desired profile or trajectory of variable values, i.e., a desired behavior of a control variable or a manipulated variable.

Control Horizon—the period of the time extending from the present into the future during which one plans to move or change manipulated variables. Beyond this horizon the MV is assumed to stay constant at its last or most recent value in the control horizon.

Prediction Horizon—the period of time extending from the present into the future during which the process or system response is monitored and compared to a desired behavior.

Cloning—the process of exercising a fundamental model over a desired range of inputs and outputs and using the results to create a neural network model.

Exemplary Biofuel Production Process

Figure 4A:
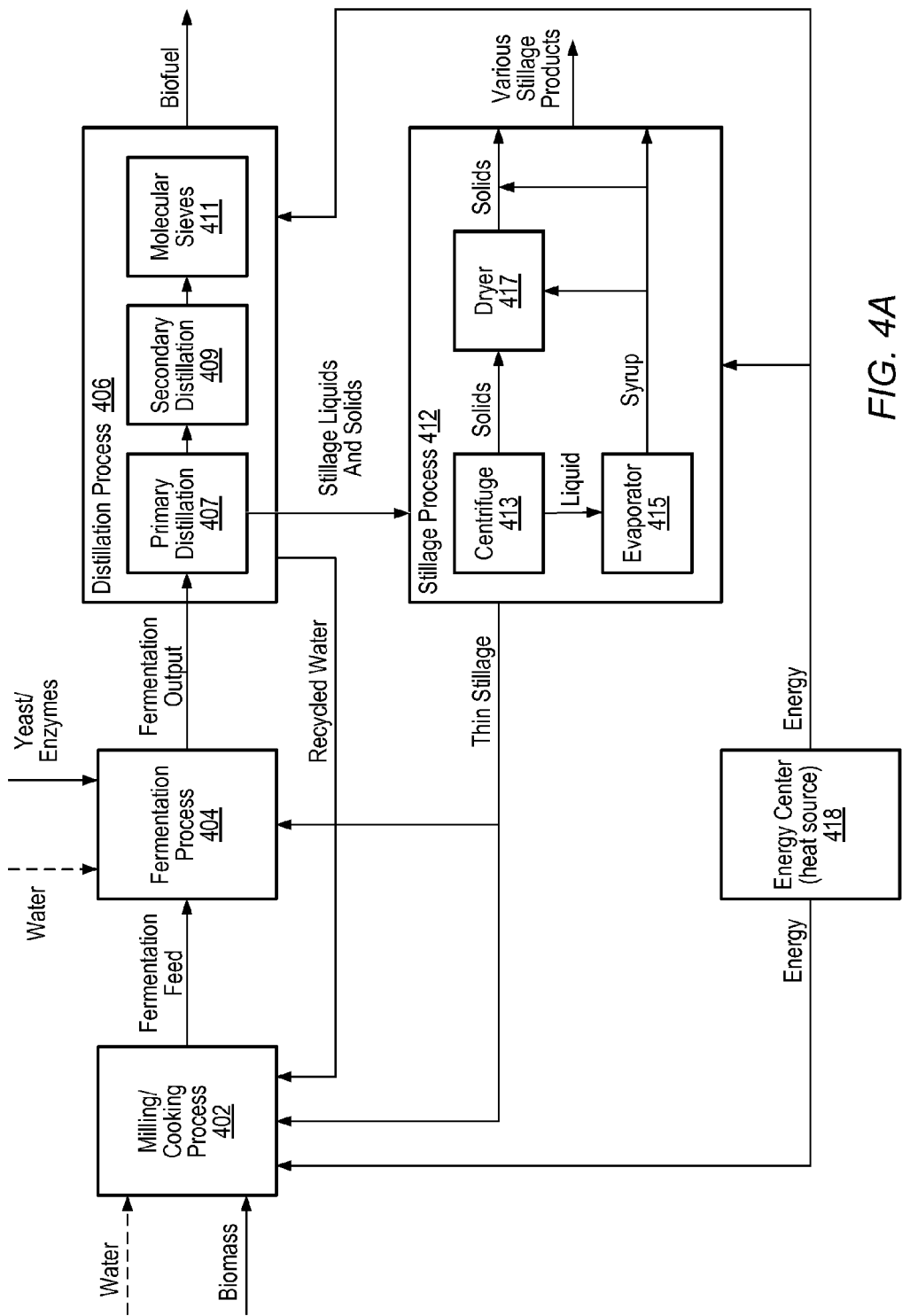
FIG. 4A illustrates an exemplary high-level processing flow schematic of plant sections of a biofuel processing plant, according to one embodiment.

FIG. 4A illustrates an exemplary high-level processing flow schematic of sub-processes of a biofuel production process, according to one embodiment. It should be noted that the particular components and sub-processes shown are meant to be exemplary only, and are not intended to limit embodiments of the invention to any particular set of components or sub-processes.

As FIG. 4A indicates, a milling/cooking sub-process 402 may: receive water, biomass, energy (electrical and/or thermal), recycled water, and/or recycled thin stillage; mill the biomass; cook the mixture; and output a biomass slurry (also referred to as a fermentation feed or a fermentation feed slurry) to a fermentation sub-process 404. The fermentation sub-process 404 may: receive the biomass slurry, recycled water, yeast, enzymes, and recycled thin stillage. The fermentation sub-process 404 may also receive additional water (not recycled). The mixture is fermented, and the fermentation products output to a distillation sub-process 406. The distillation sub-process 406 may: receive the fermentation products, remove water and stillage (liquid and solid stillage) from the fermentation products in a one to three step process (e.g., primary distillation 407, secondary distillation 409, and/or molecular sieves (or dryers) 411), recycle water removed from the fermentation products to the milling/cooking sub-process 402, output the liquid and solid stillage to a stillage sub-process 412, and output biofuel products. The stillage sub-process 412 may: receive the liquid and solid stillage, process the liquid and solid stillage (utilizing one or more of centrifuge dryers 413, other dryers 417, and/or evaporators 415) to produce and output various stillage products, and recycle thin stillage liquid to the fermentation sub-process 404 and the milling/cooking sub-process 402. An energy center 418 may provide electric power and heat (steam) to the various sub-processes as shown in FIG. 4A.

Exemplary Batch Fermentation Process

Figure 4B:
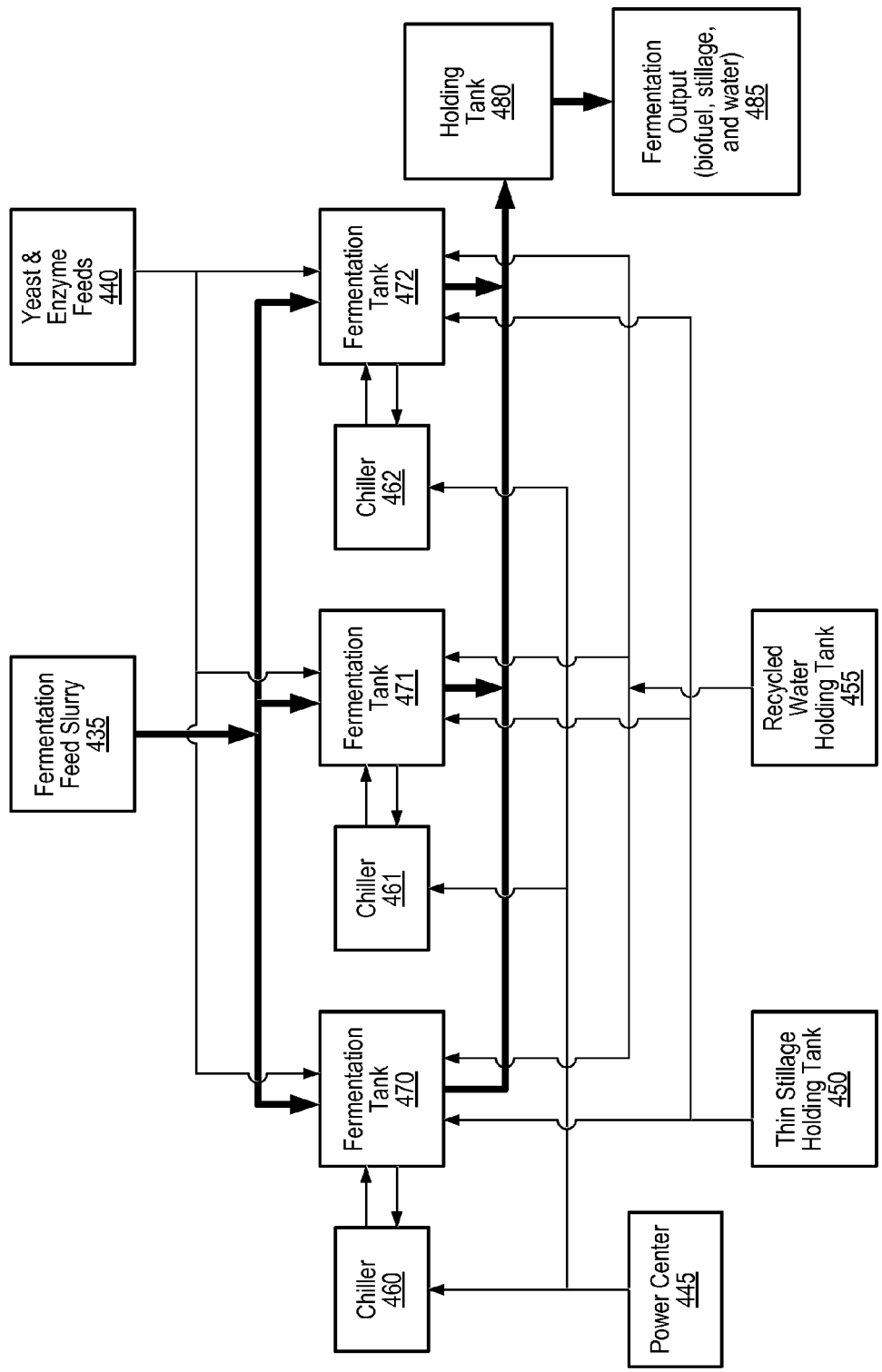
FIG. 4B is a high-level block diagram of a fermentation process of a biofuel production process, according to one embodiment.

FIG. 4B illustrates an exemplary high-level processing flow schematic of a fermentation process (e.g., fermentation process 404 in FIG. 4A) of a biofuel production process, according to one embodiment. It should be noted that the particular components or sub-processes shown are meant to be exemplary only, and are not intended to limit embodiments of the invention to any particular set of components or sub-processes.

The fermentation process equipment may include a single fermentation tank, a few fermentation tanks (e.g., the three tanks 470-472 shown in FIG. 4B), or many fermentation tanks, depending on the size of the biofuel production plant. One or more chillers 460-462 may be coupled to the fermentation tanks and provide cooling to the fermenting slurry inside the fermentation tanks through heat exchangers. Electric power may be provided to the chillers 460-462 (and various pumps, controllers, and sensors—not shown in FIG. 4B) from an energy center 445.

The fermentation process is typically a batch process, and each batch has a filling period, a fermentation period, and an emptying period. The fermentation period begins with the introduction of yeast to the tanks (yeast and enzyme feeds 440), and overlaps the filling period. The fermentation period may continue through a portion of the emptying period until the yeast is effectively depleted. The initiation time of a batch for each fermentation tank may be staggered, so that 1) the tanks are filling at different times in order to optimally utilize the fermentation feed slurry provided to the fermentation tanks from the milling/cooking process 402; and 2) the fermentation tanks are emptying at different times into the one or more holding tanks 480 (some embodiments may have multiple holding tanks 480) to optimize the size of the one or more holding tanks 480.

Thin stillage may be added to the fermentation tanks 470-472 from one or more thin stillage holding tanks 450. Thin stillage may be provided from the stillage process 412.

Recycled water may be added to the fermentation tanks 470-472 from one or more recycled water holding tanks 455. Recycled water may be provided from the distillation process 406. Additional water may be added from other sources as needed.

The fermentation process output (biofuel, stillage, and water) 485 is sent to holding tanks for the distillation process 406.

Figure 4C:
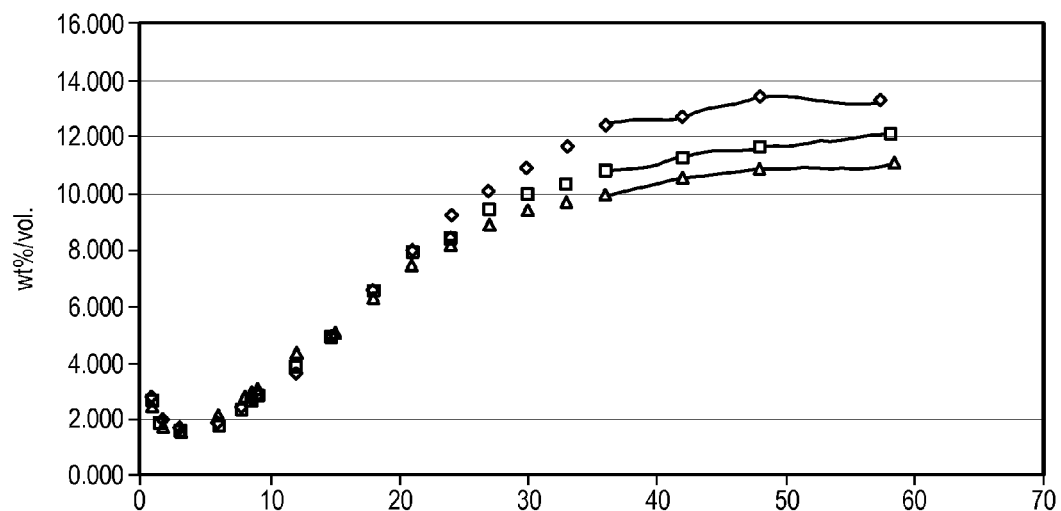
FIG. 4C illustrates an exemplary plot of ethanol concentrations as a function of batch time for three separate fermentation batches, according to one embodiment.
Figure 4D:
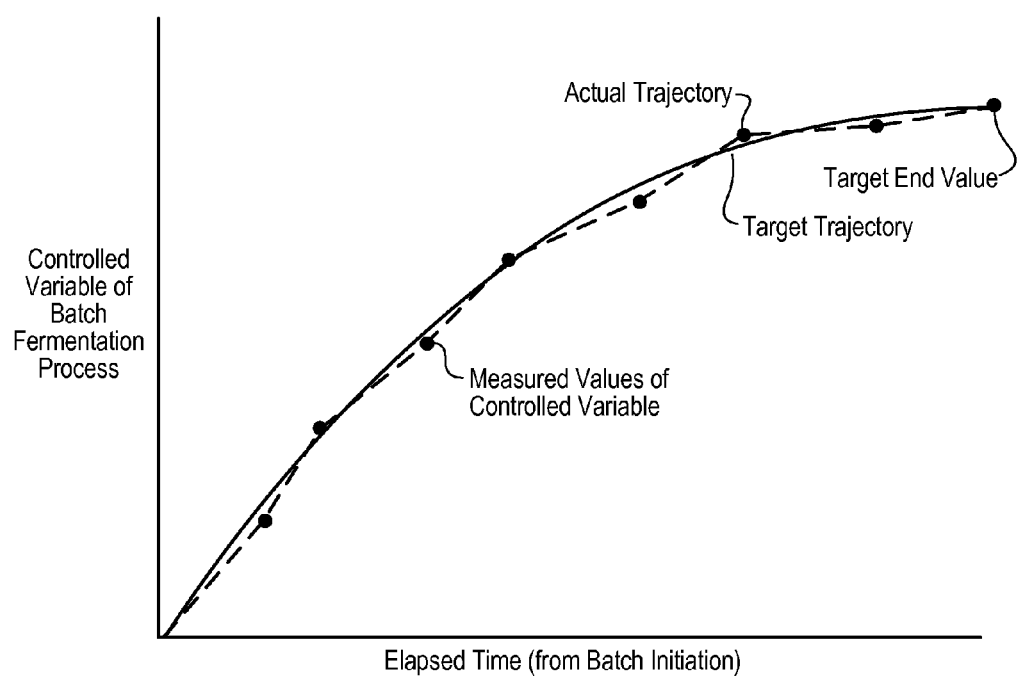
FIG. 4D illustrates an exemplary target trajectory compared to an exemplary actual trajectory for a controlled variable of a batch fermentation process, according to one embodiment.

Control of the fermentation process 404 may be achieved by adjusting the values of manipulated variables of a batch fermentation and monitoring the subsequent changes in one or more controlled variables of the batch fermentation. FIG. 4C illustrates one control variable (biofuel concentration) measured for several fermentation batches, and illustrates the variability of the fermentation process. FIG. 4D illustrates control of the fermentation process to an optimized target trajectory for a controlled variable of the fermentation batch (e.g., biofuel concentration), and the actual trajectory achieved by adjusting values for the manipulated variables during the batch process. The fermentation process may be managed and controlled via model predictive control (MPC) utilizing a dynamic multivariate predictive model that may be incorporated as a process model in a dynamic predictive model-based controller. Model predictive control of the fermentation process (also referred to as a fermentation sub-process) of a biofuel production process is described below in more detail.

MPC Applied to the Batch Fermentation Process

Various embodiments of systems and methods for applying model predictive control (MPC) to a biofuel production process are described below. In this approach to biofuel production, a dynamic multivariate predictive model may be incorporated as a process model in a dynamic predictive model-based controller. This MPC system may project or predict what will happen in the production process (e.g., in the near future) based on the dynamic prediction model and recent process history, including, for example, recent operating conditions or state values. This projection or prediction may be updated or biased based on received current process information, specified objectives, and/or system or method constraints. Control algorithms may be used to recursively or iteratively estimate the best current and future control adjustments on the model inputs to achieve a desired output path. Targets set on the dynamic model outputs may be compared to how that output may behave over a predictive future horizon and the best available controllable model input adjustments may be estimated to best achieve the controller targets.

It should be noted that the biofuel produced by embodiments of the methods described herein may be any biofuel generated from biomass, and that the types of biomass contemplated may be of any type desired, including, but not limited to, grains (e.g., corn, wheat, rye, rice, etc.), vegetables (e.g., potatoes, beats, etc.), canes (e.g., sugarcane, sorghum, etc.), and other recently living organisms and/or their bi-products.

Figure 5:
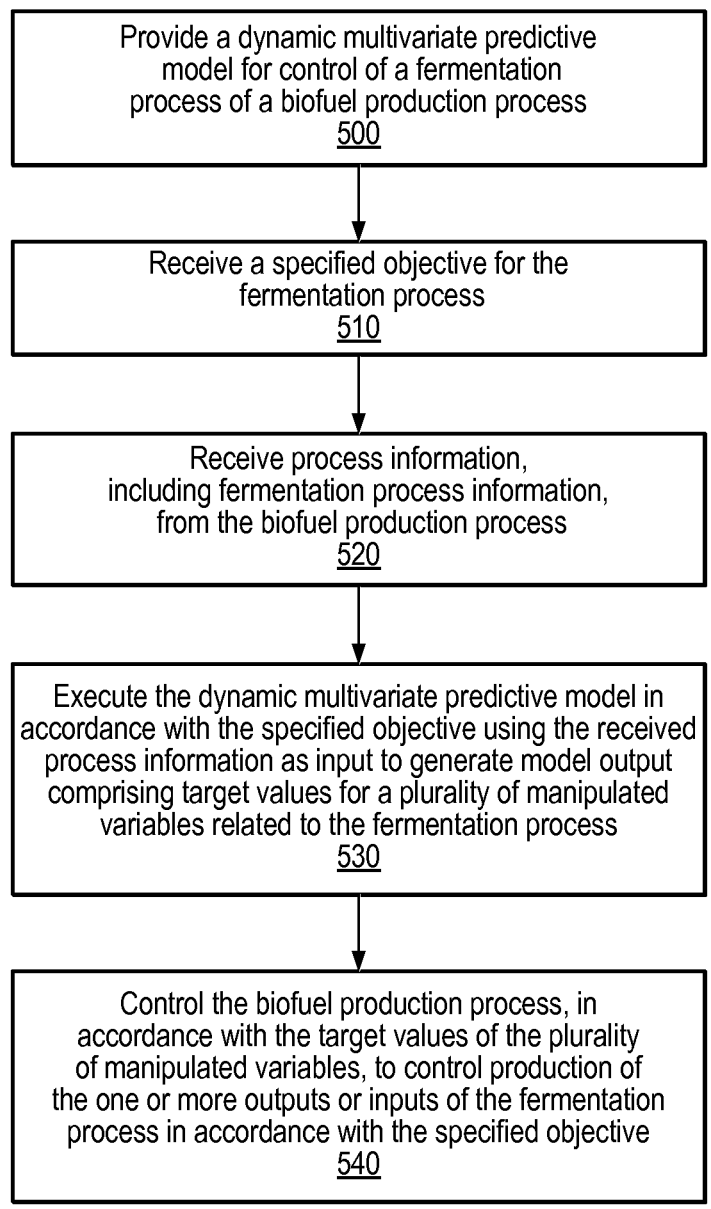
FIG. 5 is a high-level flowchart of a method for managing a fermentation process of a biofuel production process utilizing model predictive control, according to one embodiment.

FIG. 5 is a high-level flowchart of a computer-implemented method for managing a fermentation process of a biofuel production process utilizing model predictive control (MPC), according to one embodiment. As used herein, the term biofuel refers to one or more biofuel products output from a biofuel production process. It should be noted that embodiments of the method of FIG. 5 may be used with respect to any sub-process of a biofuel production process desired (e.g., milling/cooking, fermentation, distillation, and/or stillage sub-processes), as well as combinations of such sub-processes. In various embodiments, some of the method elements shown may be performed concurrently, in a different order than shown, or may be omitted. Additional method elements may also be performed as desired. As shown, this method may operate as follows.

In 502, a dynamic multivariate predictive model (also referred to as a dynamic predictive model) of a fermentation process of a biofuel production process may be provided. In other words, a model may be provided that specifies or represents relationships between attributes or variables related to the fermentation process, including relationships between inputs to the fermentation process and resulting outputs of the fermentation process. Note that the model variables may also include aspects or attributes of other processes or sub-processes that have bearing on or that influence operations of the fermentation process.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard MPC models (i.e., fitted models generated by functional fit of data), or hybrid models using any combination of the above models.

In 504, an objective for the fermentation process may be received. The objective may specify a desired outcome, result, behavior, or state, of the fermentation process, such as, for example, a desired throughput, quality, efficiency, product profile, behavior, or cost, among others. In some embodiments, the objective may specify at least one targeted measurable attribute defining product quality for the fermentation process (or the overall production process). Note that an objective may be a specific value, such as a specified percent solids for a fermentation feed, a specified temperature of a fermentation vat, etc., or may be a specified extremum, i.e., a maximum or minimum of an attribute, such as, for example, minimizing cost, maximizing production, etc.

It should be noted that as used herein, the terms "maximum", "minimum", and "optimum", may refer respectively to "substantially maximum", "substantially minimum", and "substantially optimum", where "substantially" indicates a value that is within some acceptable tolerance of the theoretical extremum, optimum, or target value. For example, in one embodiment, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations the control system will generally attempt to achieve optimum operation, i.e., operate at a targeted value or constraint (max or min) as closely as possible.

Moreover, in some embodiments, an objective may include multiple components, i.e., may actually comprise a plurality of objectives and sub-objectives. In some embodiments, the objective may involve multiple variables, e.g., a ratio of variables. Moreover, in some embodiments, there may be a global objective, e.g., maximize production or profit, and multiple sub-objectives that may in some cases be at odds with the global objective and/or one another.

In 506, process information for the fermentation process of the biofuel production process may be received. This information may be received from the fermentation process, from other portions of the biofuel production process that influence the fermentation process, and/or from other sources, e.g., a laboratory, inferred property models (that model variables that are not readily measurable), sometimes referred to as virtual online analyzers (VOAs), external systems, or any other source as desired. This information generally includes data from one or more sensors monitoring conditions of and in the fermentation process (e.g., temperatures, pressures, flow rates, equipment settings, and so forth), although any other information germane to the fermentation process may be included as desired (e.g., constraints to which the fermentation process may be subject, ambient conditions of the biofuel process, economic or market data, and so forth).

In 508, the model may be executed in accordance with the objective for the fermentation process using the received process information as input, to generate model output comprising target values for one or more manipulated variables related to the fermentation process in accordance with the objective for the fermentation process. In other words, the model may be executed with the received process information as input, and may determine target values of one or more controllable attributes of the fermentation process in an attempt to meet the specified objective for the fermentation process (which could be a global objective for the entire biofuel production process). For example, in an embodiment where the objective is to maximize biofuel output for the fermentation process, the model may determine various target values (e.g., fermentation feed input flows, temperatures, pressures, and so forth) that may operate to maximize the output. As another example, in an embodiment where the objective is to minimize waste for the fermentation process, the model may determine target values that may operate to minimize waste for the fermentation process, possibly at the expense of total biofuel output. In a further example, the objective may be to maximize profit for the entire production process, where maximizing output and minimizing waste may be two, possibly competing, sub-objectives, e.g., included in the objective.

In some embodiments, the execution of the model in 508 may include executing the model in an iterative manner, e.g., via an optimizer, e.g., a nonlinear optimizer, varying manipulated variable values (which are a subset of the model inputs) and assessing the resulting model outputs and objective function, to determine values of the manipulated variables that satisfy the objective subject to one or more constraints, e.g., that optimize the sub-process subject to the constraints, thereby determining the target values for the manipulated variables.

In 510, the fermentation process of the biofuel production process may be controlled in accordance with the corresponding targets and objective for the fermentation process. Said another way, a controller coupled to the dynamic multivariate predictive model may automatically control various (controllable) aspects or variables of the fermentation process according to the target values output by the predictive model to attempt to achieve the specified objective.

The method of FIG. 5 may be repeated, e.g., at a specified frequency, or in response to specified events, so that the process may be monitored and controlled throughout a production process, or throughout a series of production processes. In some embodiments, the period or frequency may be programmed or varied during the production process (e.g., an initial portion of a production process may have longer repetition periods (lower frequency), and a critical portion of a production process may have shorter repetition periods (higher frequency)).

In some embodiments, a system implementing the control techniques disclosed herein may include a computer system with one or more processors, and may include or be coupled to at least one memory medium (which may include a plurality of memory media), where the memory medium stores program instructions according to embodiments of the present invention. In various embodiments, the controller(s) discussed herein may be implemented on a single computer system communicatively coupled to the biofuel plant, or may be distributed across two or more computer systems, e.g., that may be situated at more than one location. In this embodiment, the multiple computer systems comprising the controller(s) may be connected via a bus or communication network.

Figure 6A:
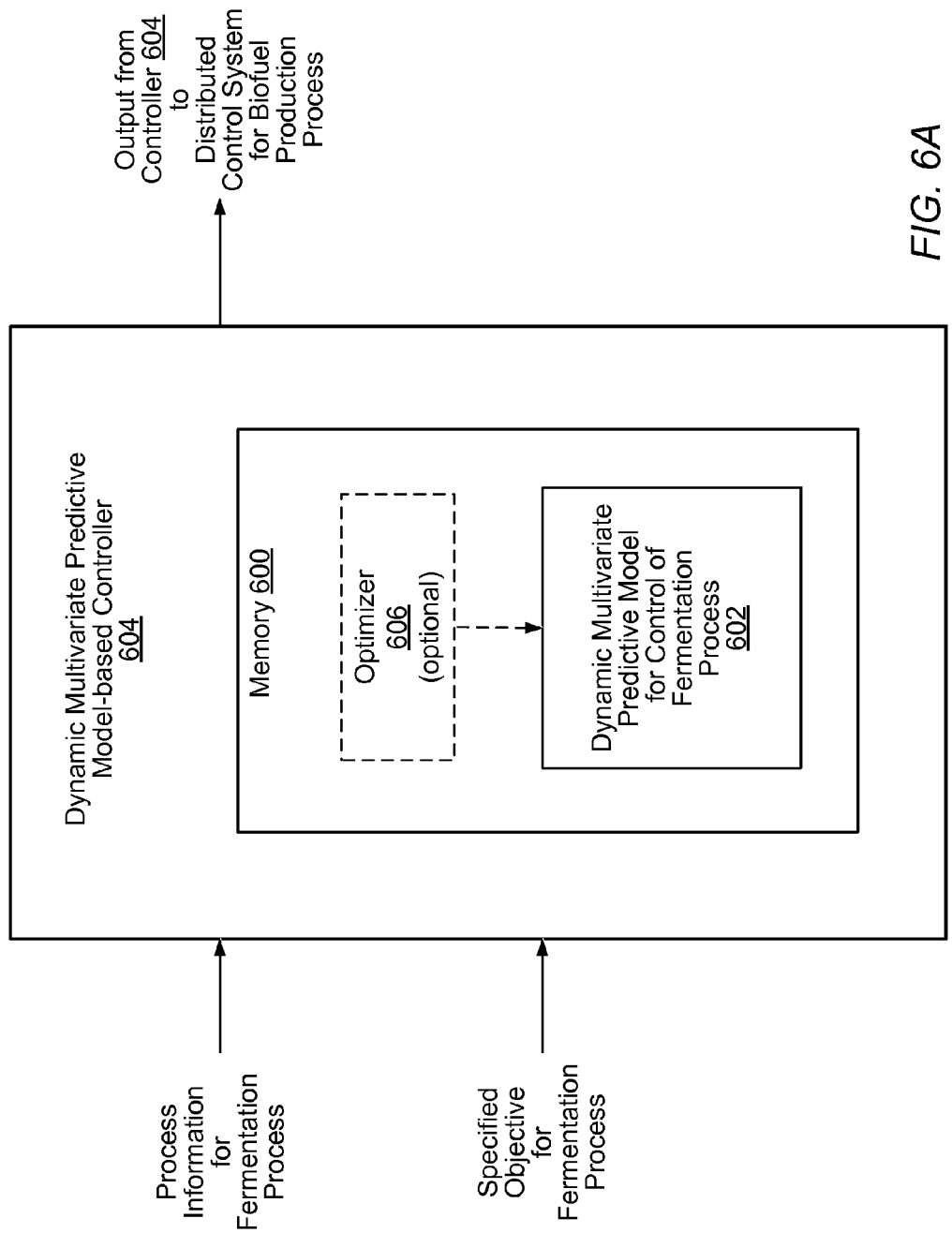
FIG. 6A is a high-level block diagram of a system for managing a fermentation process of a biofuel production process utilizing model predictive control, according to one embodiment.

FIG. 6A illustrates an exemplary system for managing a fermentation process of a biofuel production process, which may implement embodiments of the method of FIG. 5. The system may comprise: 1) a dynamic multivariate predictive model 602 (e.g., a predictive control model of a fermentation process in the biofuel production process) stored in a memory medium 600; and 2) a dynamic predictive model-based controller 604 coupled to the memory medium 600.

As described above in more detail with respect to FIG. 5, the controller 604 may be operable to: receive an objective for a fermentation process, receive process information related to the fermentation process from the biofuel production process (possibly including information from a laboratory and/or inferred property models), execute the model in accordance with the objective for the fermentation process using the received corresponding process information as input, to generate model output comprising target values for one or more variables related to the fermentation process in accordance with the objective for the fermentation process. In addition, as described above with respect to FIG. 5 in more detail, the dynamic predictive model-based controller 604 may control the fermentation process of the biofuel production process in accordance with the corresponding targets and objective for the fermentation process.

In one embodiment, the controller 604 may output the target values to a distributed control system (not shown in FIG. 7A) for the biofuel production plant. In some embodiments, the target values may include or be one or more trajectories of values over a time horizon, e.g., over a prediction or control horizon. Process information may include measurements of a plurality of process variables for the fermentation process and other inter-related sub-processes, information on one or more constraints, and/or information about one or more disturbance variables related to the fermentation process. Process information may be received from the distributed control system for the biofuel plant, entered by an operator, or provided by a program. For example, in addition to values read (by sensors) from the actual process, the process information may include laboratory results, and output from inferred property models, e.g., virtual online analyzers (VOAs), among other information sources.

In some embodiments, the memory medium 600 may be part of the controller 604. In other embodiments, the memory medium 600 may be separated from the controller 604 and connected via a bus or a communication network. In one embodiment, the memory medium 600 may include a plurality of memory media, with different portions of the model 602 stored in two or more of the memory media, e.g., via a storage area network, or other distributed system.

Figure 6B:
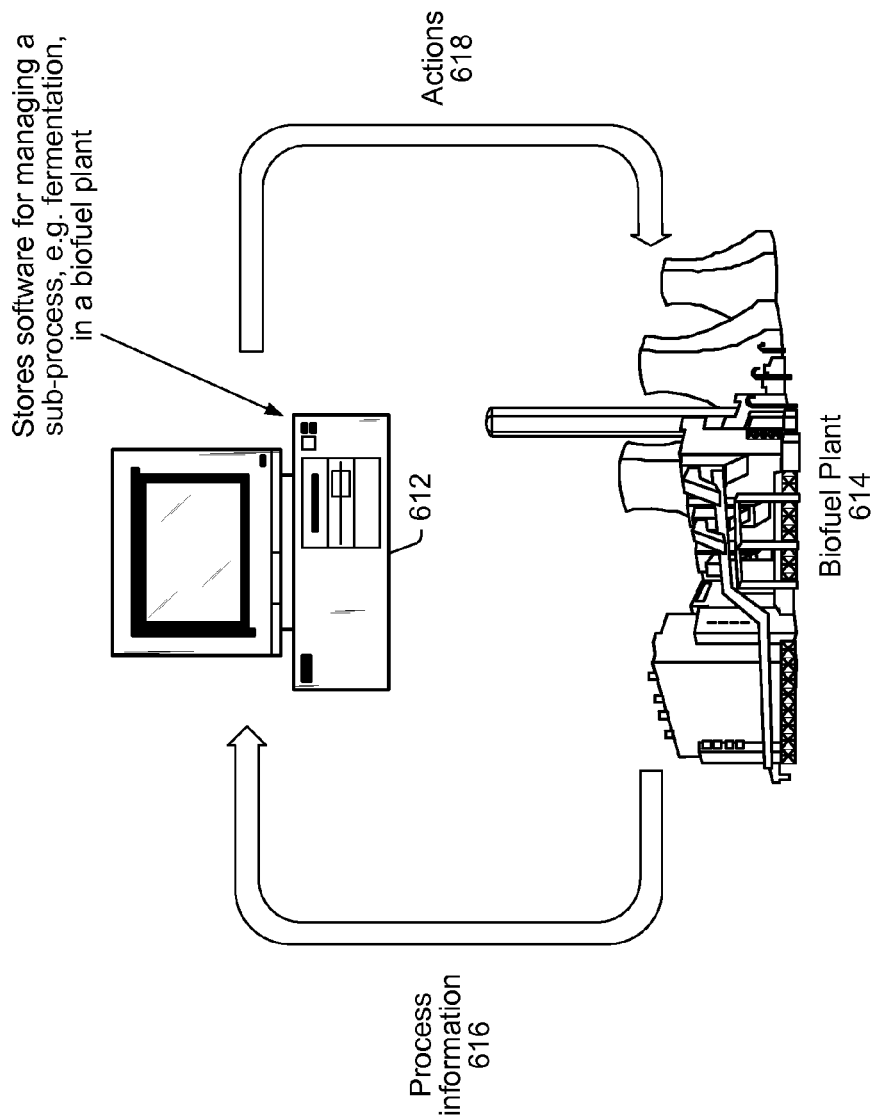
FIG. 6B is a high-level diagram of a control system for managing a biofuel production process utilizing model predictive control, according to one embodiment.

FIG. 6B illustrates a simplified view of an automated control system for a biofuel production plant 614. As shown, the system may include one or more computer systems 612 which interact with the biofuel plant 614 being controlled. The computer system 612 may represent any of various types of computer systems or networks of computer systems, which execute software program(s) according to various embodiments of the invention. As indicated, the computer system stores (and executes) software for managing a sub-process, e.g., fermentation, in the biofuel plant 614. The software program(s) may perform various aspects of modeling, prediction, optimization and/or control of the fermentation process. Thus, the automated control system may implement predictive model control of the fermentation process in the biofuel plant or process. The system may further provide an environment for making optimal decisions using an optimization solver, i.e., an optimizer, and carrying out those decisions, e.g., to control the plant.

One or more software programs that perform modeling, prediction, optimization and/or control of the plant 614 (particularly, the sub-processes, e.g., fermentation process) may be included in the computer system 612. Thus, the system may provide an environment for a scheduling process of programmatically retrieving process information 616 relevant to the fermentation process of the plant, and generating actions 618, e.g., control actions, to control the fermentation process, and possibly other processes and aspects of the biofuel plant or process.

The one or more computer systems 612 preferably include a memory medium on which computer programs according to the present invention are stored. The term "memory medium" is intended to include various types of memory or storage, including an installation medium, e.g., a CD-ROM, or floppy disks, a computer system memory or random access memory such as DRAM, SRAM, EDO RAM, Rambus RAM, etc., or a non-volatile memory such as a magnetic medium, e.g., a hard drive, or optical storage. The memory medium may comprise other types of memory as well, or combinations thereof. In addition, the memory medium may be located in a first computer in which the programs are executed, or may be located in a second different computer, which connects to the first computer over a network. In the latter instance, the second computer provides the program instructions to the first computer for execution.

Also, the computer system(s) 612 may take various forms, including a personal computer system, mainframe computer system, workstation, network appliance, Internet appliance or other device. In general, the term "computer system" can be broadly defined to encompass any device (or collection of devices) having a processor (or processors), which executes instructions from a memory medium.

The memory medium (which may include a plurality of memory media) preferably stores one or more software programs for performing various aspects of model predictive control and optimization. The software program(s) are preferably implemented using component-based techniques and/or object-oriented techniques. For example, the software program may be implemented using ActiveX controls, C++ objects, Java objects, Microsoft Foundation Classes (MFC), or other technologies or methodologies, as desired. A CPU, such as the host CPU, executing code and data from the memory medium comprises a means for creating and executing the software program according to the methods or flowcharts described below. In some embodiments, the one or more computer systems may implement one or more controllers, as noted above.

Dual Model Control of a Batch Fermentation Process

Figure 7:
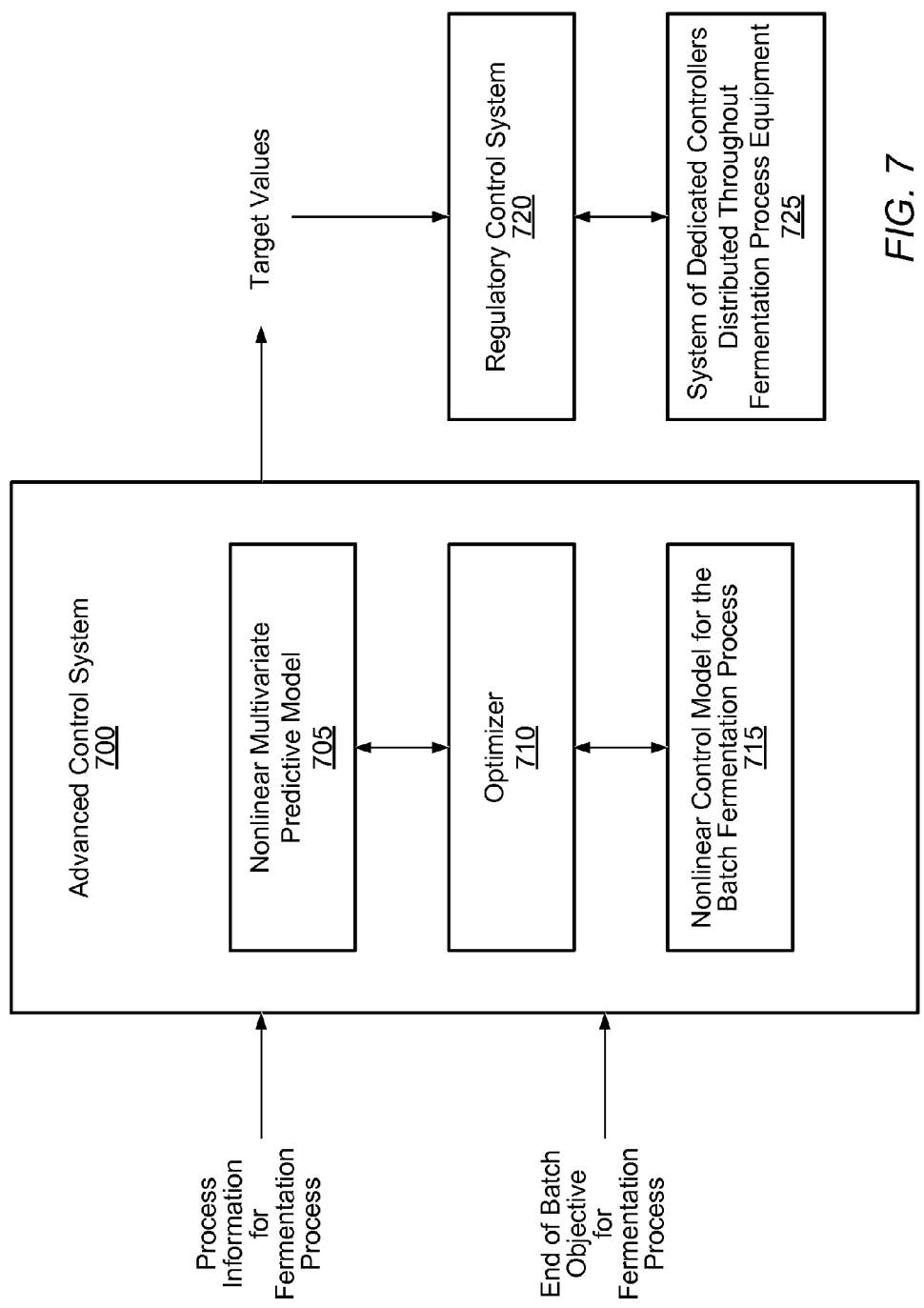
FIG. 7 is a high-level block diagram of a system for managing a fermentation process of a biofuel production process utilizing a nonlinear predictive model and a nonlinear control model, according to one embodiment.
Figure 8:
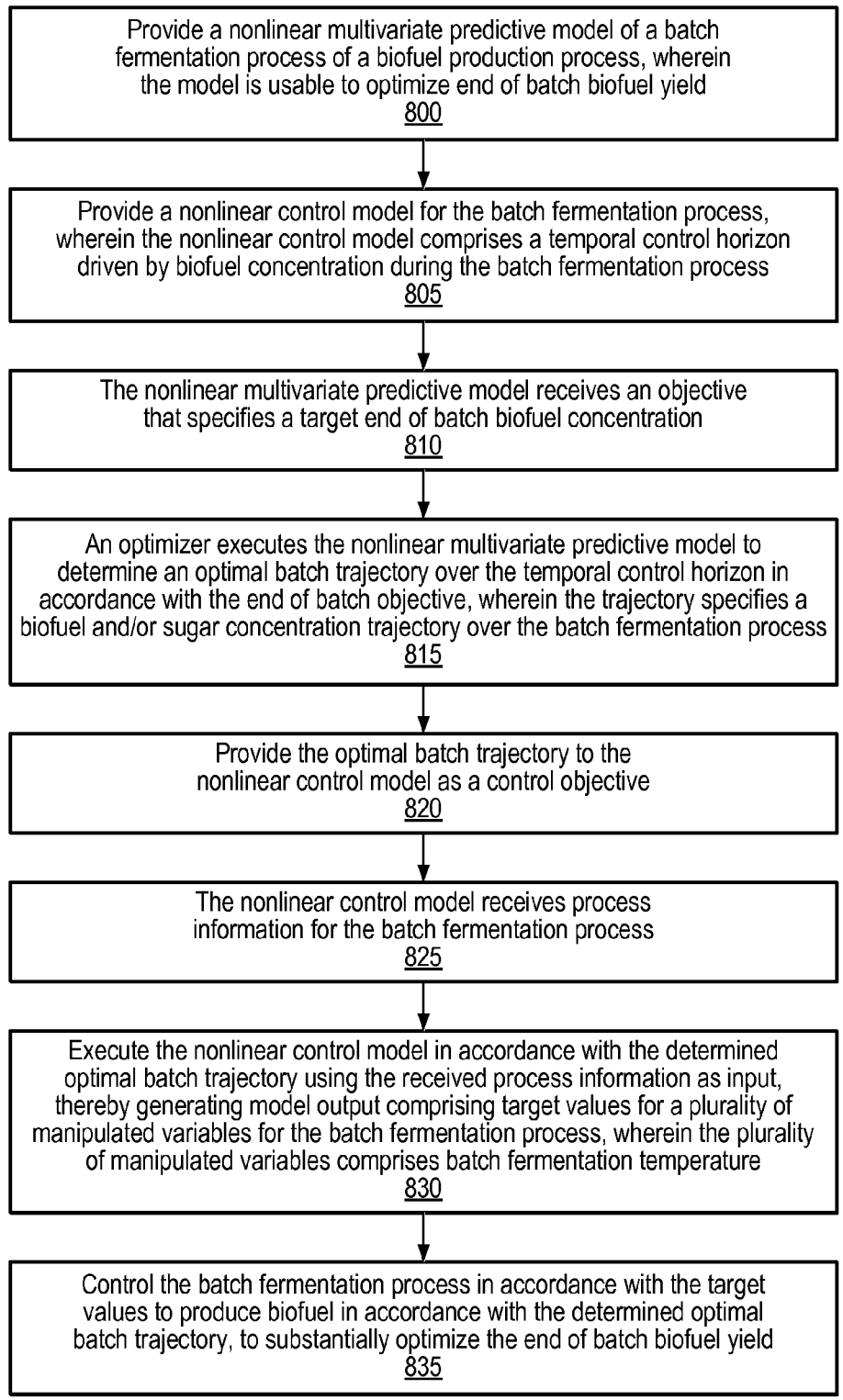
FIG. 8 is a high-level flowchart of a method for managing a fermentation process of a biofuel production process utilizing a nonlinear predictive model and a nonlinear control model, according to one embodiment.

The following describes preferred embodiments utilizing two nonlinear models to control a fermentation process of a biofuel production process according to the system of FIG. 7 and method of FIG. 8, as well as additional embodiments of model predictive control applied to a fermentation process. The various systems and methods described use nonlinear models to perform model predictive control to improve the yield, throughput, and/or energy efficiency of the fermentation process, in accordance with specified objectives. These objectives may be set and various portions of the process controlled substantially continuously to provide real-time control of the production process. The control actions may be subject to or limited by plant and/or external constraints. In some embodiments, an operating objective for the fermentation process may include operation of the fermentation tanks at an economically optimum targeted fermentation feed rate, i.e., to an economic control objective, and within constraints, such as product quality constraints, process constraints, and/or environmental constraints, among others.

Note, however, that the particular embodiments of the fermentation process described are meant to be exemplary, and that model predictive control may be applied to other embodiments of the above described fermentation process of the biofuel production process as desired.

FIGS. 7 and 8 are directed to control of a fermentation process in a biofuel production process (e.g., the fermentation process 404 in FIG. 4A). More specifically, FIG. 7 is a high-level block diagram of one embodiment of a system, and FIG. 8 is a high-level flowchart of one embodiment of a method for management of the fermentation process utilizing a nonlinear predictive model and a nonlinear control model to manage end of batch biofuel concentration and/or other objectives of the fermentation process in a biofuel production process.

Note that any of the operations and controllable variables of the fermentation process may be managed or controlled using nonlinear models and/or model predictive control techniques. Below are described various exemplary systems and methods for doing so, although it should be noted that the particular operations and variables discussed are meant to be exemplary, and that any other aspects of the fermentation process may also be managed using model predictive control as desired.

FIG. 7—Dual Model System for Control of a Batch Fermentation Process

As shown in FIG. 7, in one embodiment, a system for management of a fermentation process of a biofuel production process may include: an advanced control system 700, including: a nonlinear multivariate predictive model 705 (also referred to herein as a nonlinear predictive model) of a batch fermentation process of a biofuel production process, where the nonlinear multivariate predictive model 705 may be usable to optimize end of batch biofuel yield; and a nonlinear control model 715 for the batch fermentation process, where the nonlinear control model 715 includes a temporal control horizon driven by biofuel concentration during the batch fermentation process; and a regulatory control system 720, coupled to the advanced control system 700, where the regulatory control system 720 may be operable to be coupled to the batch fermentation process of the biofuel production process.

The advanced control system 700 may be operable to: receive an end of batch objective for the nonlinear multivariate predictive model 705, where the end of batch objective may specify a target end of batch biofuel concentration; utilize an optimizer 710 to execute the nonlinear multivariate predictive model 705 to determine an optimal batch trajectory over the temporal control horizon in accordance with the end of batch objective, where the optimal batch trajectory may specify a biofuel concentration and/or sugar concentration trajectory over the batch fermentation process; provide the optimal batch trajectory to the nonlinear control model 715 as a control objective; receive process information for the batch fermentation process; and execute the nonlinear control model 715 in accordance with the determined optimal batch trajectory using the received process information as input, thereby generating model output including target values for a plurality of manipulated variables for the batch fermentation process, where the plurality of manipulated variables includes batch fermentation temperature.

The regulatory control system 720 may be operable to control the batch fermentation process in accordance with the target values to produce biofuel in accordance with the determined optimal batch trajectory to substantially optimize the end of batch biofuel yield.

Embodiments of the model predictive control (MPC) techniques described herein may facilitate this best-case (i.e., optimal or near-optimal) achievement of projected future events, and may also enable multivariate balancing, so that, for example, levels across a series of tanks (e.g., fermentation output holding tanks) may be controlled to achieve optimal or near optimal results within process (and/or other, e.g., economic, regulatory, etc.) constraints even with a transient imbalance due to coordination of batch (e.g., fermentation) and continuous (e.g., stillage) operations. An MPC solution may have relative weighting factors to balance trade offs between competing objectives. For example, a tank level may be allowed to swing relatively freely within safe or comfortable operating regions (e.g., a tank level that is not nearly empty or nearing overflow). However, if a tank level forecast estimates that it may be nearly empty or near to over-filling, then different limit weighting may be used to avoid exceeding safe or comfortable operating states.

FIG. 8—Dual Model Method for Control of a Batch Fermentation Process

Embodiments of a method for management of a fermentation process of a biofuel production process are presented below. In one embodiment, as illustrated in FIG. 8, a method for managing a batch fermentation process in a biofuel production process, may include: providing a nonlinear multivariate predictive model 705 (also referred to as a nonlinear predictive model) of a batch fermentation process of a biofuel production process, where the nonlinear predictive model 705 may be usable to optimize end of batch biofuel yield 800; providing a nonlinear control model 715 for the batch fermentation process, where the nonlinear control model 715 may include a temporal control horizon driven by biofuel concentration during the batch fermentation process 805; and the nonlinear predictive model 705 may receive an end of batch objective, where the end of batch objective may specify a target end of batch biofuel concentration 810.

The method may further include: an optimizer 710 executing the nonlinear predictive model 705 to determine an optimal batch trajectory over the temporal control horizon in accordance with the end of batch objective, where the optimal batch trajectory may specify a biofuel concentration and/or sugar concentration trajectory over the batch fermentation process 815; providing the optimal batch trajectory to the nonlinear control model 715 as a control objective 820; and receiving process information for the batch fermentation process 825.

The method may further include: executing the nonlinear control model 715 in accordance with the determined optimal batch trajectory using the received process information as input, thereby generating model output including target values for a plurality of manipulated variables for the batch fermentation process, where the plurality of manipulated variables includes batch fermentation temperature 830; and controlling the batch fermentation process in accordance with the target values to produce biofuel in accordance with the determined optimal batch trajectory, to substantially optimize the end of batch biofuel yield 835.

Various embodiments of the method briefly described above are discussed below in more detail, again, following FIG. 8, which is a high-level flowchart of a computer-implemented method for managing a fermentation process of a biofuel production process utilizing nonlinear models and/or model predictive control (MPC), according to one embodiment. In various embodiments, some of the method elements shown may be performed concurrently, in a different order than shown, or may be omitted. Additional method elements may also be performed as desired. This method may operate as follows.

Provide A Nonlinear Predictive Model

In 800 of FIG. 8, a nonlinear predictive model for the fermentation process may be provided. In other words, a model may be provided that specifies or represents relationships between attributes, inputs, and/or other variables of the fermentation process as to biofuel concentration of the fermentation output. Note that the model variables may also include aspects or attributes of other sub-processes that have bearing on or that influence operations of the fermentation process.

Potential models may be of any of a variety of types. For example, the model may be linear or nonlinear, although for many complex processes, a nonlinear model may be preferred. Other model types contemplated include fundamental or analytical models (i.e., functional physics-based models, also referred to as first-principles models), empirical models (such as neural networks or support vector machines), rule-based models, statistical models, standard MPC models (i.e., fitted models generated by functional fit of data), or hybrid models using any combination of the above models. For example, in some embodiments where a hybrid approach is used, the dynamic multivariate predictive model may include a fundamental model (e.g., a model based on chemical and/or physical equations) plus one or more of: a linear empirical model, a nonlinear empirical model, a neural network, a support vector machine, a statistical model, a rule-based model, or an otherwise empirically fitted model As is well known to those of skill in the art of predictive models, a dynamic multivariate predictive model may include a set of process mathematical relationships that includes steady state relationships, and also includes any time lag relationships for each parameter change to be realized. A great variety of dynamic relationships may be possible, and each relationship between variables may characterize or capture how one variable affects another, and also how fast the affects occur or how soon an effect will be observed at another location.

Predictive Models for Batch Fermentation Process

The development of dynamic predictive models for management of a batch fermentation process is discussed below.

In one embodiment, the method may manage or implement a temperature profile throughout the batch biofuel fermentation process to achieve an optimal or targeted biofuel production trajectory, via a batch fermentation dynamic prediction model of biofuel production as a function of one or more of yeast addition parameters, temperature profile, biomass concentration, and/or pH, among others.

One embodiment of a MPC based batch fermentation model may relate changes in batch processing input information (particularly temperature, which may be a critical controllable variable throughout a batch) to biofuel production. Some examples of such input information are provided in the following comments. Yeast addition parameters may include information about both biofuel producing organism quantity (e.g. yeast concentration) and activity. Such information may be measured (frequently in a manually acquired sample tested in a laboratory, although occasionally online by turbidity or optical density measurements that may be related to cell concentrations), inferred from propagation, inferred from mass spectroscopy information on fermentation tank exhaust gas (e.g. oxygen uptake rate, carbon dioxide exhaust rate) or by direct addition information (e.g., values may be obtained from fermentation batches directly inoculated with dried yeast or active yeast slurry), among other techniques. Temperature measurements may also be acquired from both the fermentation feed during filling (potentially including liquefaction and/or saccharification temperatures) and a direct measurement of fermentation processing temperature. These temperatures may influence yeast viability, activity, and enzyme activity. Biomass concentration parameters may include the amount of biomass (e.g. yeast nutrient and feedstock amounts available to convert to biofuel) that may be added to the fermentation tank during filling. Acidity, i.e., pH, measurements may include one or more measurements made during the process steps of: liquefaction, saccharification, and/or filling, and/or developing pH values during the batch cycle. Relationships between these pH measurements and yeast viability, production, and enzyme activity may be determined.

Note that while the potential model inputs have influences on many of the critical batch production performance parameters, many of these influences may be independent (e.g. increasing temperature may increase cell death more than growth, even while increasing enzyme activity and nutrition availability to cells). In these relationships, a nonlinear model may be utilized because many of these dependencies may have varied responses at different times during a batch cycle (e.g. cells may become sensitized to higher biofuel concentrations later in a batch cycle, and/or cells may be more temperature tolerant at the beginning of a batch). In addition, enzyme activity, although dependent on temperature may have changing dependencies at varying pH levels.

The complex nature of these biological systems present challenges for model development. In general a more accurate model may provide more complete and accurate relationships between what may be changed (e.g. fermentation temperature, pH, etc.) and what may result from these changes (e.g., biofuel production). Consequently, it may be assumed that a simple model provided with plant operations information (e.g., controller options) may perform better than repeatedly applying the same recipe, e.g., traditional "rules of thumb". Since biomass quality changes, plant operating limits (e.g., equipment capability) change, ambient conditions change, plant economics change (e.g., biomass costs, biofuel costs, processing/energy costs, and by-product demand and costs may change), a fermentation model may perform better if developed with certain methodologies.

An empirical model may be derived directly from past plant performance data, and may represent or encode empirical relationships of the process. There are various ways to develop such a model, but the first priority may be to ensure that non-linear features of the model are based on accurately observed relationships between what may be changed or manipulated and what may result. To achieve such accuracy with empirical modeling, a nonlinear modeling methodology (e.g., artificial neural networks) may provide an advantage. It is rare that such a model can be developed without some plant experimentation, and so either before or during model development, the significant modeled input parameters that can be tested should be tested. Because of the complexity of the described model (e.g., number of potential inputs) the developing may utilize available plant test data and supplement these test data with selective testing on high priority variables, e.g., biomass solids (batch-to-batch), temperature (within several batches), enzyme addition (both batch-to-batch and within several batches) and initial yeast concentrations (batch-to-batch), and so forth.

Some fundamental model relationships may also be used from the available prior art, such as, for example:

1. "A kinetic model and simulation of starch saccharification and simultaneous ethanol fermentation by amyloglucosidase and *Zymomonas mobilis*", Bioprocess Engineering 7 (1992), pp 335-341.

2. "Evolutionary Optimization of an Industrial Batch Fermentation Process", Anres-Toro, et. al, University of Madrid, Spain.

3. Internal Paper, "Optimal Temperature Control for Batch Beer Fermentation", Biotechnol. & Bioeng., 31, pp 224-234 (1988).

These references are hereby incorporated by reference in their entirety as though fully and completely set forth herein. It should be noted, however, that the models disclosed in these references are not intended to limit the invention to any particular model or type of model.

The following is such a model for the lag phase (i.e., the propagation tank), per the above references:

Lag Phase (Propagation Tank) (1)

$$y_{active} + y_{lag} = a_i y_{initial}$$

$$\frac{dy_{active}}{dt} = \mu_{lag}(a_l y_{initial} - y_{active})$$

-continued $$\mu_{lag} = \alpha_{lag} e^{\left(\frac{-\beta_{lag}}{T}\right)}$$

$$\frac{dy_{lag}}{dt} = -\mu_{lag} y_{lag}$$

$$\frac{dy_{active}}{dt} = \mu_{lag}(a_l y_{initial} - y_{active})$$

$$\mu_{lag} = \alpha_{lag} e^{\left(\frac{-\beta_{lag}}{T}\right)}$$

$$\frac{dy_{active}}{dt} = \mu_{lag}(a_i y_{initial} - y_{active})$$

$$\mu_{lag} = \alpha_{lag} e^{\left(\frac{-\beta_{lag}}{T}\right)}$$

Fermentation Phase

A fundamental model of at least a portion of a fermentation process is represented by the equations above. The following describes some model options that may be utilized. The fermentation process equations may be broken into two phases: the lag phase and the fermentation phase. The lag phase may represent the period of time the yeast takes to get accustomed to its environment. Lag may primarily occur in a propagation tank, although some lag may be exhibited in the fermentation tank as the growing yeast becomes adaptive to a higher glucose environment.

Several important factors of the fermentation process may be used to modify the published (prior art) models:

1. A significant amount of the fermentation may occur as the fermentation tank fills. The model may thus need to take into account the changing volume of the tank during this filling process step. This may be equally critical in optional processes where fermenter volume may be limited to restrict peak cooling demand due to heat exchange capacity.

2. Slurry may be fed into the fermentation tank for the first approximately 12-18 hours, thereby constantly changing the carbohydrate concentration. For this reason, biomass volume may need to be integrated during the filling step as well as during the remainder of the batch process.

3. Dextrins may be broken down to glucose due to the addition of Glucoamylase into the fermenter and yeast propagation (e.g. simultaneous saccharification).

4. The slurry feed may consist mostly of DP4-range sugars due to the addition of an amylase in upstream processing.

One exemplary embodiment of the invention may be achieved by addressing the features 1 through 4 discussed above by modifying some fundamental relationships to provide a kinetic model in the form of modeled equations (relationships), constraints, and definitions presented below.

A. Volumetric Change in the Fermentation Tank $$\frac{dV}{dt} = F_{slurry} \quad (2)$$

$$F_{slurry} = 0 \text{ when } t > t_{Fill}$$

B. Activation of Yeast $$\frac{dy_{Lag}}{dt} = \left(-\mu_{Lag} - \frac{F_{slurry}}{V}\right) y_{Lag} \quad (3)$$

$$\mu_{Lag} = \text{conversion rate} = f(T)$$

C. Growth of Yeast $$\frac{dy_{active}}{dt} = \left(\mu_x - r_d - \frac{F_{slurry}}{V}\right)y_{active} + \mu_{lag}y_{lag} \quad (4)$$

$\mu_x = \text{growth rate} = \dfrac{\mu_x^{max} y_{sugar}}{k_x - y_{EtOH}}$ (modified Michaelis-Menten function)

$\mu_x^{max} = \text{theoretical maximum growth rate} = f(T)$ $k_x = \text{saturation constant} = f(T)$ $r_d = \text{death rate} = f(T)$

D. Death of Yeast $$\frac{dy_{dead}}{dt} = r_d y_{active} - \frac{F_{slurry}}{V} y_{dead} \quad (5)$$

$r_d = \text{death rate} = f(T)$

E. Conversion of Sugars $$\frac{dy_{sugar}}{dt} = r_{GA} y_{Dex} - \mu_s y_{active} - \frac{F_{slurry}}{V} y_{sugar} \quad (6)$$

$r_{GA} = \text{conversion of dextrins to glucose by Glucoamylase}$ $\mu_s = \text{conversion rate} = \dfrac{\mu_s^{max} y_{sugar}}{k_s - y_{sugar}}$ (Michaelis-Menten function, Monad kinetics)

$\mu_s^{max} = \text{theoretical maximum growth rate} = f(T)$ $k_s = \text{saturation constant} = f(T)$

F. Production of Ethanol $$\frac{dy_{EtOH}}{dt} = \mu_a f_a y_{active} - \frac{F_{slurry}}{V} y_{EtOH} \quad (7)$$

$\mu_a = \text{conversion rate} = \dfrac{\mu_a^{max} y_{sugar}}{k_s - y_{sugar}}$ (Michaelis-Menten function, Monad kinetics)

$\mu_a^{max} = \text{theoretical maximum growth rate} = f(T)$ $k_s = \text{saturation constant} = f(T)$ $f_a = \text{inhibition factor} = (1 - \alpha y_{EtOH})$

G. Dextrin Conversion $$\frac{dy_{Dex}}{dt} = \frac{F_{slurry}}{V}(y_{Dex}^{IN} - y_{Dex}) - r_{GA} y_{dex} \quad (8)$$

$y_{Dex}^{IN} = \text{sugar concentration in feed stream}$ $r_{GA} = $ conversion rate short-chain sugars to glucose by Glucoamylase

H. Temperature Dependence $$f(T) = \alpha e^{\left(-\frac{\beta}{T}\right)} \quad (9)$$

Note that in the above equations, concentrations are given as mass/volume—the standard way HPLC (high purity liquid chromatography) data are represented when biofuel alcohol facilities monitor and report fermentation progress. Note further that the published coefficients in the incorporated articles cited above may be basically unusable because the intensive operating conditions of a commodity biofuel plant may be well outside the developed range of these equations and the yeast and enzyme performance may be regularly evolving due to the competitive business environment of the field of biofuel production (e.g., evolving to process speeds where documented academic models no longer maintain relevance).

In general, the form of the equations may be useful for the optimization solutions described herein, and the greatest model uncertainty may be yeast activity. Consequently, a fundamental model may be biased to a measured biofuel production by adjusting a multiplier on the yeast concentration and may be an effective way to adapt fundamental modeling for this application.

In some embodiments, the fermentation model may be a hybrid combination of the fundamental modeling equations with adjusted parameters (e.g., the parameters of the equations that may be poorly represented in the prior art with respect to currently operated intensive biofuel production). Hybrid or parametric constrained training of empirical modeling may be accomplished with existing empirical modeling, fitting or other techniques, and may be implemented based on historic plant data and limited plant testing data (e.g., a subset of the above variables recommended for testing within the empirical modeling) and used to calculate coefficients as a function of T and/or pH (e.g., for the example equations provided above these variables may include: $\mu_{lag}$, $\mu_x^{max}$, $k_x$, $r_d$, $\mu_s^{max}$, $k_s$, $r_{GA}$, $\mu_a^{max}$, $k_a$, and/or $\alpha_a$, among others).

Hybrid (e.g. combined empirical and fundamental) modeling may use the model equations A through H above, calculate the various coefficients with available data to fit a best model, within measured and/or historic performance. In general, empirical techniques may be used in this manner to match measured relationships with fundamental equations (e.g., the fundamental literature models were developed from pilot plant experiments). Artificial neural network or other empirical modeling techniques may be used to manage and coordinate data from various sources, limit the identified range of these parameters, and may use nonlinear or linear relationships where appropriate (e.g., where a parameter may be a function of temperature). These tools may be helpful, in development of a fermentation model. The fermentation model may be developed using fundamental, empirical or a combination of these techniques as described.

In some embodiments, the predictive model may be created from a combination of relationships based on available data such as: vessel volumes and fundamental dynamic and gain relationships, sufficiently available and moving plant historic process data, and supplementary plant testing on variables that cannot be identified from the two previous steps. In one embodiment, the nonlinear multivariate predictive model may be a function of two or more of: yeast influence, temperature, biomass concentration, enzyme concentration, batch progress, and/or pH. The yeast influence may include one or more of yeast concentration, yeast addition, or yeast activity, among other yeast-related parameters.

Models may be customized to the plant layout and design, critical inventories, plant constraints and measurements, and controllers available to manage variables. Moreover, in some embodiments, external factors, such as economic or regulatory factors, may be included or represented in the model. In preferred embodiments, the predictive model may be a nonlinear multivariable predictive model.

An important characteristic of a predictive model may be to identify when a control variable will change as a result of a change in one or more manipulated variables. In other words, the model may identify the time-response (e.g., time lag) of one or more attributes of the fermentation process with respect to changes in manipulated variables. For example, once a controller adjusts pump speeds there may be a certain time-dependent response before observing an effect at a tank being filled. This time-dependent response may be unique for each independent controller (i.e., flow rates may vary because of differences in system variables (e.g., piping lengths, tank volumes, etc.) between the control actuator and flow sensor and the pump location).

In one embodiment, the predictive model may include inferential models (also referred to as property approximators or virtual online analyzers (VOAs)). An inferential model is a computer-based model that calculates inferred quality properties from one or more inputs of other measured properties (e.g., process temperature(s), flow(s), pressure(s), concentration(s), level(s), etc.). In one embodiment, the predictive model may be subdivided into different portions, and stored in a plurality of memory media. The memory media may be situated in different locations of the biofuel plant. The controller may communicate with the memory media utilizing a communication system.

Provide A Nonlinear Control Model

In 805 of FIG. 8, a nonlinear control model for the fermentation process may be provided to utilize MPC to achieve real-time batch adjustment to stay on a quality based trajectory (a trajectory for optimum values of a quality variable throughout a fermentation batch). In other words, a nonlinear model may be provided that specifies or represents relationships between attributes, inputs, and/or other variables of the fermentation process in order to provide continuous (or periodic) batch adjustments to stay on a control variable trajectory provided by the predictive model (e.g., a biofuel concentration trajectory). Note that the model variables may also include aspects, attributes, or variables of other sub-processes that have bearing on or that influence operations of the fermentation process.

There may also be fermentation process disturbances (not subject to control) that may be unmeasured or even unmeasurable. For example, consider a situation where a level starts to rise out of balance with filling demand, e.g., because of manual plant changes (e.g., scheduled equipment cleaning that involves draining and/or filling one or more specific tanks)—the control model may be made aware of an imbalance so that corrective actions may be made gradually to avoid dramatic or critical consequences. This may be an issue for many of the tanks that have both batch and continuous plant operations in sequence. Specific tanks may be used to provide storage capacity to facilitate balancing and avoid continuous out-of-control operations after every batch action. Because batch vessels drain rapidly, specific tank levels may be difficult to maintain in automatic level control. Thus, real-time receipt of current vessel and material balance information (flows and levels) may provide an update on current equipment status and the execution of the dynamic model may enable projections to be made to avoid both emptying/over-filling vessels and emergency large flow moves to correct imbalances.

In one embodiment, the control model may include inferential models (also referred to as property approximators or virtual online analyzers (VOAs)). An inferential model is a computer-based model that calculates inferred quality properties from one or more inputs of other measured properties (e.g., process temperature(s), flow(s), pressure(s), concentration(s), level(s), etc.). In one embodiment, the predictive model may be subdivided into different portions, and stored in a plurality of memory media. The memory media may be situated in different locations of the biofuel plant. The controller may communicate with the memory media utilizing a communication system.

In one embodiment, a nonlinear control model may be developed that may manage each batch to the targeted biofuel production trajectory (e.g., temperature dependent batch-time or ethanol concentration influence on ethanol production). This controller may be based on the relationships of the prediction models as in the "MPC Management of Fermentation Temperature Staging Utilizing a Batch Model" subsection above. Thus the nonlinear effect of temperature on ethanol production may be common between the model and the controller. From this information, tuned to the plant performance, exchanger capacity may be described in past data. Measured, inferred, or off-line modeled qualities (biofuel concentration, sugar concentration, or other quality attribute) may be used to more directly control temperature staging to achieve improved fermentation results.

In designing such a controller it may be critical to configure/design a method whereby batch measurements may be received related to biofuel production. In general, a real-time controller may have real-time feedback that may inform the control application that it may be performing on the desired trajectory. In this case, the biofuel concentration, volume, or mass may not generally be measured in real-time, but may be intermittently sampled by manual operator samples and HPLC results in a production unit laboratory. There may be several solutions for this requirement. First an online analyzer may be installed and several industrial FT-NIR instruments may meet the requirements of such an analyzer. A second option may be to use the fermentation models with intermittent feedback, i.e., without real-time feedback, with direct data entry as manual laboratory samples are provided. In this case the model as incorporated in the controller may run with intermittent feedback (e.g., as when the controller predicts the process response perfectly) until an intermittent data entry occurs. This may be an improvement over current manual control methods performed by an operator, who may make manual temperature adjustments after a number of manual samples indicate that fermentation may need adjustment. In this case, a more comprehensive control model may provide better control through a better defined relationship between biofuel production and variables such as temperature, fermentation feed biomass, yeast addition, and others. In the intermediate case, an inferred property model may be developed using various empirical and fundamental model forms that may provide a more accurate prediction of biofuel production than the control model and this may be used in the interim between manual laboratory sampling and data entry to gradually adjust the controller in a feedback basis. In this case, the inferred property model may be using not only input parameters to the controller, but also various state and other process measurement indicators of fermentation performance (e.g., cooling water exchanger duty) to more accurately calculate biofuel production between manual samples.

In this case, when manual samples are taken and made available to the model, the samples may be used to intelligently bias the inferred property model that provides continuous feedback to the controller.

In one embodiment, an important function of the control model may be to receive and use a trajectory of targets or operating constraints. Because of the scale of a large biofuel fermentation tank, temperature control has significant dynamic capacitance (e.g., the fermentation tank temperature responds slowly). In this case, model-predictive control may match controller feedback to a future trajectory and may attempt to maintain not only the current biofuel production to target, but also the future horizon of biofuel production. A trajectory of targets and in some cases constraint limits may be very useful in improved controller performance.

In one embodiment, a key objective of this controller may be to maintain an optimum production trajectory (or sugar removal trajectory) rather than a temperature staging path. As this may be directly aligned with the objective of the fermentation process (biofuel production rather than temperature control) significantly higher performance on each batch, much closer to a consistently best performance may be achieved. This may occur even under limitations produced by regularly changing processing conditions and economic operating drivers.

Receive an Objective Specifying End of Batch Biofuel Concentration

In 810 of FIG. 8, the nonlinear predictive model may receive an objective specifying end of batch biofuel concentration.

In one embodiment, the specified objective may include one or more of: one or more operator specified objectives; one or more programmable objectives; a set of target fermentation feed rates to the fermentation tanks; one or more cost objectives; one or more product quality objectives; one or more equipment maintenance objectives; one or more equipment repair objectives; one or more equipment replacement objectives; one or more economic objectives; one or more objectives in response to emergency occurrences; one or more dynamic changes in product inventory information; one or more dynamic changes in product quality information; and/or one or more dynamic changes in one or more constraints on the biofuel production process, among others.

In some embodiments, other control variables may be specified (e.g., biofuel volume, concentration, etc.). Thus, the specified objective for the fermentation process may include a desired behavior, attribute, or result of the fermentation process (e.g., at least one targeted measurable or model-able attribute defining product quality for the fermentation process output). The objective may be computer generated or input by plant personnel, i.e., the objective for the fermentation process may be specified by a human operator and/or a program, and may involve a variety of sub-process units in a variety of combinations depending on the specific plant and be subject to a variety of process, equipment, safety and environmental constraints. The objective may impact the product yield, throughput, and/or energy efficiency of the fermentation process.

In some embodiments, the objective may include one or more sub-objectives. In some embodiments, the specified objective may be or include an objective function that may specify a set of objective values or relationships corresponding to each of one or more sub-objectives.

Determine Optimal Batch Trajectories with an Optimizer

In 815 of FIG. 8, an optimizer may execute the nonlinear predictive model in an iterative manner to determine an optimum batch trajectory over a temporal time horizon in accordance with the end of batch objective, where the trajectory specifies a biofuel and/or sugar concentration trajectory over the batch fermentation process. The optimizer may be included in, or invoked by, the advanced controller.

In various embodiments, any of various optimization techniques may be applied to the above models. For example, a model of batch end ethanol concentration as a function of biomass mass, fermentation temperature staging, enzyme usage, and batch time may be used to calculate biofuel production (e.g., volume or % biofuel) as a gradient or global optimization function to maximize the following equations or a sub-set thereof:

$$(\% \text{ Biofuel} * \text{Fermenter Volume})/(\text{Batch Time} * \text{Biofuel Volumetric cost})$$

$$\% \text{ Biofuel} * \text{Fermenter Volume})/(\text{Batch Time} * \text{Specific Processing Energy cost})$$

$$\text{Biomass Mass}/(\text{Time} * \text{Biomass Cost/unit mass})$$

$$\text{Enzyme Addition}/(\text{Time} * \text{Enzyme Cost/unit added})$$

In one embodiment, a more comprehensive optimization approach may be to use a more detailed hybrid model, or any of the above (empirical or fundamental) fermentation models, to calculate a globally optimum dynamic optimization across possible combinations of batch trajectories. The driving economics may be as straightforward as the above equations or more complex based on more specific options. In the best case, the equations may be constrained by global plant constraints and may be updated in real time or intermittently in real time (limited by CPU capability). However, some optimization methods may be too noisy for real-time optimization, in which case, smoother mathematics, optimization penalties for large unexpected moves, and/or an optimization technique that may be less aggressive (e.g., than genetic algorithms) may be preferred.

In one embodiment, the dynamic prediction model described above may be incorporated as a process model in a model-based dynamic control system (MPC). The MPC system may project what will happen based on the dynamic prediction model and recent process history. This projection may be updated or biased based on the currently received process information and the control algorithms may be used to recursively estimate the best current and future control moves on the model inputs to achieve a desired output path. Thus targets set on the dynamic model outputs may be compared to what that output may do over a predictive future horizon and the best available controllable model input moves may be estimated to best achieve the controller targets. In this case, targets on biofuel production may be calculated by estimating the best current and future moves regarding fermentation temperature. Because of the long dynamics and process lag within large volume fermenters, model-based control may have significant advantages in attempting to approach targeted biofuel production throughout a batch (e.g. wt %, gallons, kg, etc.).

In one embodiment, the controller or MPC as described above may calculate the future best moves and implement the current moves on each controllable setpoint. In this case, the objective may be a pure reaction balance control system, and many regulatory controllers that deploy the solution may be flow controllers, temperature controllers, or other configured regulatory controllers, that adjust flows (e.g., enzyme flows, cooling water valve positions, or specific controller outputs that may be valve positions for material flow). The current calculated best moves may be written to the regulatory control system (DCS, SCADA, and/or PLC) and these moves may be made to the process.

In some embodiments, a 'controllable' regulatory controller may be enabled for remote setpoint adjustment, generally with a switch that can be adjusted by plant personnel. If a controller may be an input to the dynamic model above, but disabled from remote setpoint adjustment, it may be assumed independent and measured as feedback from the above receipt of process information. Any 'controllable' input may be calculated and adjusted by changes and communication with parameters in the regulatory control system. This solution may write to these parameters through a control system interface (API) and the control system may implement the changes.

This may be critical because the plant changes and the "best moves" may change from instant to instant or within the execution frequency of the MPC system. If a monitored level or biomass solids changes, or has an offset from the predicted 'best' result and control change may be deployed then the best case may be implemented in the plant. This control action frequency may be set up so that many gradual adjustments may be made to provide a stable operating environment. The material flows, fermentation end concentrations, and temperatures may be relatively stable—as compared to manual operation. Ultimately even with continual, but gradual adjustments to the process targets the principal objective may be that fermentation yields may be balanced with changing process conditions (e.g., better or worse corn qualities, changing processing limits, and/or yeast activity) so that during the operation of a fermentation process, there may be a relatively constant yield of biofuel, residue sugars, and/or by-products, and a relatively constant cycle time.

The model-based controller described above may control biofuel concentration (or biofuel volume or mass within a fermenter—e.g., gal or kg ethanol). This concentration may be increasing over the batch, and a controller that may only be targeted at the batch end (e.g., 12% from the beginning) may tend to take the current relationship between temperature and biofuel concentration and increase or decrease temperature to its control limits. There may be several ways to manage this, and in general may involve using a batch trajectory either on the target (recommended) or on the constraint limits (e.g., changing temperature limits over the batch, or changing sugar/dextrin concentrations over the batch, or changing temperature control valve limits over the batch). The ultimate intent of this requirement may be that the batch control management has varying targets throughout the batch. An algorithmic solution may be provided to manage these changing objectives.

In one embodiment, the recommended methodology may be to use a targeted biofuel concentration (or mass, or volume) trajectory. Controlling the biofuel production and identifying an optimal/best-case trajectory may be the most robust (e.g., flexible, responsive, and reactive) method as batches that require more cooling may be corrected on temperature, while still approaching targeted yields at the targeted batch cycle time. Trajectories may be passed to a dynamic model-based controller either directly as target (or set point) trajectories, so that the controller sees the changing trajectory of the target over the controller's prediction horizon, or at a minimum as a current target only with a frequent update (one fifth of the batch cycle time or faster) to the current target. There may be an advantage to use target trajectories over the control model-prediction horizon (this may be the controller's future prediction time within which target errors may be integrated and minimized by calculated control action). With target trajectories, the current and future targets may be represented within the control horizon, and temperature or other control moves may be made to stay on target as much as possible within this entire prediction window. A single constant target covering multiple hours of increasing biofuel concentration may cause the controller to over- or under-shoot this target trajectory.

In one embodiment, a second trajectory-based method using constant biofuel concentration may be to limit some other part of the control variable element within a changing trajectory across the batch target. For example, temperature limits may be used based on the dynamic model's forecasted temperature trajectory to achieve substantially optimal biofuel concentration at the end of the batch. In this way a constant, end-of-batch, target biofuel concentration may be used, but temperature (or cooling valve(s)) would be limited so that they do not over-respond to achieve batch targeted responses. A constant temperature limit may not be expected, but one that varies during the batch. This has the disadvantage that batch performance changes may not be evident within the controller and if biofuel production falls behind, something external to the controller may need to change the temperature (etc.) limits or performance would suffer.

In another embodiment, a third approach may be used. Specifically, a fully dynamic batch controller model may be used that calculates and controls to an optimal trajectory within the model.

Provide Optimal Batch Trajectory to the Nonlinear Control Model

In 820 of FIG. 8, the optimal batch trajectory determined by the optimizer may be provided to the nonlinear control model to be used as a control objective. In other words, the optimizer may execute the nonlinear multivariate predictive model (iteratively) to determine the (substantially) optimal batch trajectory per the specified objective (e.g., to maximize end of batch biofuel concentration), and this trajectory may then be provided to the nonlinear control model as a control objective.

Receive Process Information

In 825 of FIG. 8, process information may be received by the nonlinear control model from the biofuel production process. The process information may include measurements of one or more control variables and one or more manipulated variables related to the batch fermentation process and one or more variables of other processes that may impact the batch fermentation process, and possibly information from inferential models, laboratory results, etc. For example, the process information may include batch temperature, cooling system temperatures, e.g., return broth temperature, cooling water temperature, etc., valve positions, tank volumes or levels, and so forth, among others. The process information may be communicated to the nonlinear control model from a distributed control system.

In some embodiments, constraint information specifying one or more constraints may also be received. For example, in some embodiments, the objective may include constraint information specifying the one or more constraints, i.e., limitations on various aspects, variables, or conditions, related to the fermentation process, although in other embodiments, the constraint information may be separate and distinct from the specified objective. In one embodiment, the constraint information may include one or more of: a constraint on sugar concentration over the batch fermentation process, or a constraint on end of batch sugar concentration.

In one embodiment, the constraint information may include dynamic constraint information, e.g., the fermentation process may be controlled in accordance with an objective, but may also be subject to dynamic constraints, e.g., constraints on or of the production facility's equipment, product qualities, its raw material costs, material availability, e.g., water constraints, production plans, product value, product market demand, and other constraints. The nonlinear control model may receive this constraint information specifying one or more constraints related to the fermentation process, and generate model output in accordance with the objective subject to the one or more constraints. The constraint information may include dynamic constraint information. In one embodiment, the one or more constraints may include one or more of: equipment constraints, capacity constraints, temperature constraints, pressure constraints, energy constraints, market constraints, economic constraints, regulatory constraints, operating limits of product markets that affect production rates of products, and/or operator imposed constraints, among others.

In some embodiments, equipment constraints may include one or more of: operating limits for various pumps, operational status of pumps, holding tank capacities, operating limits for various control valves, operating limits for valve temperatures, operating limits for pipe pressures, operating temperature limits of equipment, operating limits of rotary equipment as measured by amperage, temperature, or other load measurement, and/or safety or environmental limitations for equipment operation. For example, in one embodiment, a constraint on operation of the fermentation feed may relate to pumping limitations on any of the various sections of the fermentation feed pumps and/or pipes. In situations where an objective is to maximize or maintain biofuel output product production rates, or biofuel product quality at certain target rates, this objective may drive a pump to its maximum or minimum limit, and the objective may then be compromised due to equipment/pump limits.

In one embodiment, the one or more equipment constraints may also include one or more of: fermentation equipment capacity limits that limit fermentation process output feed rates to the primary distillation units; equipment constraints that limit thin stillage feed rates or capacity from the stillage process; operating limits for one or more pumps in the thin stillage feed; operational status of pumps (online or offline); thin stillage tank capacities; holding tank level limits that limit feed rates to the fermentation tanks; operating limits for tank pressures; operational status of tanks; pump speed, valve position, or other controller output limits within the primary distillation or fermentation systems; operating limits for valve pressures; operating limits for valve temperatures; equipment amp limits; among others.

In some embodiments, the optimal batch trajectory over the temporal control horizon may be determined subject to the at least one constraint. Similarly, in some embodiments, the target values for the plurality of manipulated variables may be determined subject to the at least one constraint.

Thus, in one embodiment, the nonlinear control model may comprise a multivariate predictive model that represents relationships between the one or more constraints, the objective, including any sub-objectives, and the plurality of manipulated variables.

Execute the Nonlinear Control Model

In 830 of FIG. 8, the nonlinear control model may be executed in accordance with the determined optimal batch trajectory using the received process information as input, thereby generating model output comprising target values for a plurality of manipulated variables related to the batch fermentation process, where the plurality of manipulated variables includes fermentation batch temperature. The target values may correspond to various manipulated variables including, but not limited to batch fermentation temperature, thin stillage flow rates, and inventories for thin-stillage recycled back to the fermentation units, among others. The nonlinear control model may be configured to generate a plurality of target values for manipulated variables simultaneously.

In some embodiments, the nonlinear control model and/or the nonlinear multivariate predictive model may be a dynamic model, which may be important because the time response during a batch may be different based on the batch response curve (typical batch profile for ethanol production). In addition, the effect of temperature on biofuel production may have complex interactions between the effect on enzyme performance (and nutrient availability) and yeast growth and death. These relationships may not be instantaneous (organisms adapt and become gradually sensitized to conditions) and may dynamically vary (e.g., have different response times) as the batch may be in different phases. The nonlinearities may arise not only from the complex interactions of enzymes and organism relationships to temperature, but also from sensitivity to nutrient and biofuel concentrations (note that the example model presented above uses the well-known fundamental Michaelis-Menten function with Monad kinetics).

Many common significant interactions and model inputs may be represented in the control model, including, for example, temperature, biomass concentration, pH, yeast conditions (activity and concentration), and current biofuel concentration (note that while not an equilibrium equation, the Michaelis-Menten functions may also be an appropriate way to represent the impact of higher ethanol concentrations on slowing batch reaction rates). These relationships, while common in represented form (empirical, fundamental or hybrid) demonstrate several significantly different design and recipe differences, including, for example: simultaneous or series saccharification (with fermentation), yeast propagation with or without aeration, and managing yeast lag phases in different ways to reduce the influence of lags on production, direct yeast addition to fermentation (no propagation) along with more finite changes with yeast strain varieties, (temperature tolerant or high-performance, more sensitive yeasts to yeast hybrids specialized for very high biomass solids concentrations), enzymes, (designed for and with various pH and temperature sensitivities), and fermentations managed with a variety of carbohydrate energy sources (sugar cane, corn, milo, other grains, and cellulose). Thus, there may not be one model common to all biofuel fermentation processes or designs. The dynamic control model may be at least in some way customized or tuned to each fermentation operations' unique process conditions.

Control the Batch Fermentation Process

In 835 of FIG. 8, the batch fermentation process may be controlled by the regulatory control system 720 in accordance with the target values to produce biofuel in accordance with the determined optimal batch trajectory, to substantially optimize the end of batch biofuel yield.

Various aspects of managing the batch fermentation process and related portions of other sub-processes in accordance with the target values and the determined optimal batch trajectory to provide real-time continuous control of the batch fermentation process are presented below. The control actions may be subject to or limited by plant and external constraints. More specifically, various embodiments of the invention may be utilized to control one or more aspects of the fermentation process and related portions of other sub-processes, including, but not limited to, one or more of: (1) feed rate to the fermentation tanks, (2) energy requirements in the chillers, (3) feed rate of recycled water from the primary distillation tower units to the fermentation tanks, and (4) feed rate of thin stillage to the fermentation process (also referred to as recycle backset % or backset recycle streams).

In one embodiment, controlling flow rates of fermentation feed to each fermentation tank by the regulatory control system 720 may involve one or more of: one or more flow controllers coupled to fermentation feeds to each fermentation tank, level sensors for one or more fermentation feed holding tanks, and/or flow sensors to measure feed rate to each of the fermentation tanks.

In one embodiment, the system may include an energy center and MPC control may be used to control the energy utilization efficiency for the batch fermentation process by regulating the energy demand. In another embodiment, MPC may be configured to control the energy center subject to environmental requirements.

In one embodiment, controlling the biofuel production process may include control of the inventory of biofuel, which may include or utilize one or more of: a measure of the inventory of one or more biofuel products, an operator or computer entered control objective for the inventory of one or more biofuel products.

In one embodiment, the control model may be used in a model-based controller that uses this model-based process to target specific best-case plant performance. As biofuel concentrations (or volume, mass) change dynamically (but not instantaneously) after changes in fermenter environment (volume, concentrations, enzymes, temperature, pH), a model-based controller may predict in real-time, not only how far, but how fast temperature or other fermenter controllers should be adjusted to move operations from current performance to target concentrations. The accuracy of the model with respect to the process (and the biofuel concentration measurement) may avoid corrections based on model error and may limit controller course corrections (e.g. batch trajectory) to those that may be real rather than course corrections that may be based on model mismatch. So while any robust controller algorithm may perform reasonably well even with model mismatch, reducing this mismatch may enable more aggressive controller action and therefore tighter control to the targeted (best) batch trajectory.

In one embodiment, a robust control algorithm may be used, e.g., to control the fermentation process. For example, any of various nonlinear control methodologies may be used, ranging from fairly frequent linear model corrections (e.g., gain scheduling (e.g., within one fifth to one tenth of a batch cycle)), to similar active controller switching (e.g., using linear controllers operating in parallel, whose results may be selected based on batch conditions) to fully nonlinear controllers of various architectures. Adaptive control may be feasible although it may be assumed that the primary model adaptation may be identified off-line and automatically adapted based on batch progression with an ability to refine any nonlinear model with adaptation as an added feature within the construct of a fairly representative batch nonlinear control model (e.g., current adaptive control model technology may be assumed to be too slow to manage the fairly continuously changing batch interactions described under the dynamic model sections described above).

Assuming that model accuracy may be relative, and that a robust control model algorithm may be used (e.g. the controller may be designed to live with and manage control within certain amounts of model uncertainty and error), dynamic control model accuracy improves performance, but may provide satisfactory fermentation control improvements across a range of sophistication and accuracy. That said, the same caveats described in the end of the dynamic model description may apply here. Control model accuracy may be the ultimate delivery mechanism of performance improvements and it may need to be sufficiently accurate to enable improved response beyond current manual operations ability within the limitations of their understanding and in this case the available amount of time to pay attention to fermentation.

As noted above, in some embodiments, MPC may allow not only this best case achievement of projected future events, but may also enable multivariate balancing so that, for example, in the case where temperature affects both yeast growth, death rates, and nutrient availability, the yeast produces ethanol as a function of temperature, nutrient level, and biofuel concentration the nonlinear interactions and therefore the 'right' temperature moves may be somewhat complex. Finally, there may be in addition, complex interactions between temperature and enzyme activity with differing relationships between yeast activity and temperature. The tradeoffs of enzyme addition and temperature staging may be most readily handled in a multivariate control solution. In such a solution, these interactions may be solved as part of the model and the best approach to the biofuel production target may be made.

Various method elements of the method of FIG. 8 may be repeated, e.g., at a specified frequency, or in response to specified events, so that the process may be monitored and controlled throughout a production process, or throughout a series of production processes. For example, in one embodiment, the above receiving process information, executing the nonlinear control model, and controlling, may be repeated in an iterative manner to achieve targeted biofuel production over a fermentation batch. In some embodiments, the repeating the executing the nonlinear control model may generate target values comprising a fermentation temperature staging profile for the fermentation batch.

In some embodiments, the period or frequency may be programmed or varied during the production process (e.g., an initial portion of a production process may have longer repetition periods (lower frequency), and a critical portion of a production process may have shorter repetition periods (higher frequency)). As mentioned above, in some embodiments, the repetition may be based at least partially on events, e.g., in response to specified conditions. In some embodiments, the receiving an objective may also be included in the repeating. In other words, the receiving an objective, receiving process information, executing the dynamic multivariate predictive model, and controlling the biofuel production process may be repeated with a specified frequency (or in response to specified events or conditions), utilizing updated process information and objectives in each repetition. The frequency may be programmable, and/or operator-determined as desired. In some embodiments, the frequency may be determined by changes in process, equipment, regulatory, and/or economic constraints.

In one embodiment, the dynamic control model may be executable to: receive biofuel concentration and batch processing information (e.g. temperature, cooling, yeast addition, biomass concentration and pH) from the biofuel production process and generate model output comprising target temperature and/or cooling to the fermentation process.

In one embodiment, the controller may be operable to control biofuel concentration or volume related to the fermentation of the biofuel production process in accordance with the targeted temperatures and/or cooling to manage the fermentation to the targeted production trajectory.

In one embodiment, a key benefit come from automatically using this dynamic model information to control each batch (e.g. each of several active batches active at any one moment in time at various stages of completion) to its best-case target. This may be accomplished by running the control model calculations in parallel to the process, updating its status as frequently as possible, including updating model inputs (e.g., temperature, cooling demand, pH, yeast addition, biomass concentration, etc.) and model outputs (e.g., biofuel concentration, concentrations of sugars) at the slowest frequency of the controller execution frequency or the controller input update frequency.

In one embodiment, the executed control model may make real-time changes throughout a batch to regularly correct the batch production path to the target. This may result in continuous performance that approaches the target and automatically assure substantially best-case results. Additionally, after managing a good series of batches at high performance the opportunity to execute the dynamic model at even better levels of performance may become evident. If, for example, increasing temperature to a maximum during some phase of the batch is a significant part of the highest batch performance, tests can be run at even higher levels (e.g. by several tenths of a degree) to determine whether higher performance is possible. In addition it may be fairly straightforward to use slightly higher biofuel trajectories over the entire batch (e.g., increase the trajectory by 0.5%*batch time/total batch cycle time) to check if the controller can find a path to an additional 0.5% yield.

In one embodiment, the model based extension of the above system to manage starch- and/or cellulosic-based fermentations to add relationships of enzyme rates (including temperature and/or pH dependencies on effectiveness) to extend the nonlinear dynamic model and control enzyme addition with temperature to manage biofuel concentration (or volume) may be used.

In one embodiment, the enzymes may be used to convert starch, dextrin, fructose and cellulose to dextrose. Based on the carbohydrate source used, specific enzymes and target enzyme ratios may be appropriate. The enzyme ratios may currently be managed either as flow (e.g. gal/min, gal/day) or ratio (gal enzyme/1000 gal slurry). In this case the enzyme may usually be added during preparation of yeast propagation, cook and fermentation filling steps. In most cases (although not inconceivable) enzyme addition may not be configured for addition within a filled fermentation. In any case, the enzyme activity may be dependent on: temperature, pH, biomass concentration, and biomass make-up (e.g., types of biomass or fractions of carbohydrate types). The described fundamental models provide sample equations for enzyme activity relationships, which interact with many of the changing fermentation parameters.

In one embodiment, a nonlinear batch production model may be developed. It may be integrated into a controller that manages both temperature and enzyme addition staging during a batch to target a best-case biofuel production trajectory. This controller may or may not in addition have constraint trajectories on sugar concentrations—particularly to avoid poor yields or high-sugar post-fermentation broth that causes operational issues (infections or handling of sticky DDG). Enzymes not only provide nutrient for yeasts to produce biofuel, they also consume sugars that may cause handling problems and may be directly related to batch yields (residual sugars). In that way a high acceptable level of residual sugars during each batch phase may not be a constant, but could be an operating constraint to assure that end of batch results may not only be on-track for biofuel production, but also on-track for batch yields. If for example, a starch with an unusually high fermentable sugars concentration may be added to fermentation—high limits on acceptable sugars would offset a lower than achievable biofuel target to improve both yields and end of batch ethanol concentrations.

In some embodiments, the enzymes may be staged (mixed at varying rates throughout a fill or batch) to stage metabolic rates. As increased metabolic rates increase energy intensity the highest period of biofuel production may be the highest demand for cooling and if cooling may be a limit—staging enzymes may be an effective way to operate within processing and yeast stress limits on temperature. As much of the highest yeast activity may be during the fill (when yeast inoculation to fermentation may be at low fermentation volumes) staging enzyme addition will not only avoid unacceptable temperature peaks (and yeast death rates), but could in very hot seasons improve overall fermentation performance.

In one embodiment, the expansion of either of the above fermentation applications to incorporate broader plant operating limits (milling, cook, distillation, DDG handling, etc.) so that the targeted biofuel trajectory may be managed on-line to maximize plant capacity, yields and/or economics. As fermentation is the direct source of biofuel production this can be managed in real-time through changing (shortening, lengthening or further adjusting) the biofuel target trajectory to increase or decrease production rates to match broader plant operating limits.

In some embodiments, where corn milling may be the plant limitation and corn cannot be milled at the current fermentation rates the fermentation trajectory can be slowed down to match current milling capacity and with such extended batch cycle-times higher biofuel yields could be attained. This could include in a similar way DDG handling limits or with slightly different options on ethanol dehydration (distillation and/or molecular sieve operations) limits. Limits on ethanol dehydration can be managed through either one or a combination of limiting fermentation cycle time and/or increasing end of batch ethanol concentration (e.g. reducing water to be removed).

In one embodiment, this extension may utilize the fermentation model in a supervisory way to coordinate continuous plant operating limits with batch processing limits. Therefore, the batch production model in this embodiment may be integrated in order to be deployed at a higher control level (e.g., sending new biofuel production trajectories to the batch controller). It integrates the batch model so that the cycle time may time an end of batch biofuel and by-product (e.g., DDG) production volume (and biomass demand) to calculate the demand and production rates. These demand and production rates may be limited by the rate-limiting plant processing step within the model (including fermentation limits as well as milling, slurry handling, biofuel dehydration and by-product, DDG, handling limits). The result of this coordination may be updated biofuel production trajectories. The result may be deployed in a control (e.g., continuously updated trajectories from the current fermentation status) or a steady-state (e.g., updated trajectories on each batch prior or at start) fashion.

In one embodiment, the methodology question of how to coordinate external processing units with a supervisory batch model to confirm the plant wide rate-limiting processing unit has a number of feasible answers. The most comprehensive methodology may be to combine the control models running on each other processing step including their constraints and critical target objectives. In this way each control model's individual limit, where it relates to plant rate limiting throughput, may be combined and represented exactly as utilized on the individual controllers. A second methodology may be to independently develop, or by reducing the individual plant section models create a united representation shortcut of the rate limiting processing steps on each processing segment (e.g., ethanol dehydration, stillage processing, milling/cook and fermentation). Where milling/cook could be represented by the calculated limit on fermentation feed rate (from a milling/cook controller), the ethanol dehydration could be represented by calculated limits on the maximum feed rate to the primary distillation column (e.g., beer stripping column) and stillage processing could be represented by calculated limits on the maximum total centrifuge feed rate. Again each of these representative limits could be calculated as a result of each plant sections controller or from a simplified (even linear) controller on each plant sections critical constraints (e.g. increasing beer column feed rate 1 gpm increases rectifier reflux pump speed, a controller output, by approximately 0.75% at it's high limit and when the reflux pump speed may be approximately 84.0% and it's maximum limit may be approximately 85%, beer feed may be within approximately (85-84%)/0.75%*1 gpm or 1.33 gpm of it's maximum). There may be in the case of noisy or rapidly swinging measurements a need to either filter the measurements (in the simplest case) or use a dynamic control model with input filtering on its prediction error update. This allows usage of the biofuel plant capacitance designed to handle measurable imbalances required for manual batch and continuous processing interactions and avoiding over-correcting batch trajectories for transient limits.

In one embodiment, the extension of plant wide coordination of batch processing within continuous processing limits may include further degrees of freedom including not only production trajectories, but also fermentation feed biomass concentration and/or fermentation fill volumes to maximize overall plant capacity, yield and/or economic optimum.

In one embodiment, increasing or decreasing biomass concentrations in fermentation feed affects both fermentation yields and production as well as specific pre- and post-fermentation processing limits. These relationships may not be identical as bio-mass concentration within a fermentation can have rate-limiting production effects based on equipment design and capabilities and any solids fed to the fermenter that may not be digested within the available fermentation cycle time will be handled within the by-production stillage processing (DDG) equipment. In addition, while the yeast propagation equipment may be configured to deliver within a certain maximum of cell concentration and activity—adjusting overall fermentation fill volumes with a relatively stable best-case inoculation concentration can shorten or extend cycle time results.

In one embodiment, ultimately the relationship between these input variable changes may and could be represented in the fermentation model. Note that where many facilities do not currently vary fermentation volume, these appears to be a limitation on process equipment management and therefore to reduce degrees of freedom that an operator needs to deal with. It can be in several cases sub-optimal—although we do not believe anyone has documented this opportunity even for manual fermentation management. If fermentation fills volume should be calculated with respect to other plant or fermentation bottlenecks it may be represented as part of the fermentation model. This may be needed in almost any case in a biofuel plant because considerable fermentation production of biofuel occurs during the fill (e.g., when volume may be varying). The fundamental equations documented above therefore provide for a varying fermentation volume.

In one embodiment, fermentation fill volume may be run to its safe maximum (e.g., based on operational practice this is generally below 100% level). With the maximum volume running up toward the Monod equation rate limiting reaction kinetics for forming biofuel the maximum design biofuel concentration can be reached and therefore maximum batch biofuel production achieved each batch. In the event that either the fill pumping capacity is limiting (e.g., fill time would be extended beyond the target of other fermenter readiness) or the mills may be limiting (fermenter may be filled, but only with more water, no more biomass) it may be better to limit the fermenter volume. In this way each fermenter may be filled to the 'optimum' or target solids concentration and a new fermenter may be utilized as rapidly as it becomes available. There does not generally appear to be an advantage to circulate more waters without biomass (e.g., fill a tank to the top with water recycled and fresh) and the dynamic models for each fermenter can be run in various cases or with optimization techniques to confirm which is best. A second reason that fill volume may be limited is that in warm summer months, fermentation cooling is limited as cooling water temperatures become higher. During the most active production period the cooling water valve (and chillers if used) saturates wide open so that no further chilling is available. Once wide-open, fermentation temperature control is no longer available and temperatures rise. As the temperatures rise beyond the target optimum trajectory they can get so high that yeast death becomes significantly higher than yeast growth and earlier than this yeast stops producing biofuel. Limiting the fermentation volume with a fixed cooling exchanger area, limited cooling water supply and temperature will reduce the volume to be cooled with the same heat exchange. This would in that even enable a much closer approach to optimum temperature targets and more importantly an ability to continue to produce biofuel. The supervisory batch management application could manage volume and its relationship to cooling demand and capacity to determining the best result on fermentation volume (e.g. when to reduce volume and cycle times), batch cycle times, biomass solids concentrations and temperature trajectory.

In one embodiment, this application may be either a supervisory (and more gradually acting) batch control application (e.g., adjusting batch trajectories on the active biofuel processing fermenters) or a steady-state batch optimization application (where batch trajectories may be adjusted to achieve an overall objective with respect to end of batch biofuel volumes, cycle times, etc., (e.g. production) with respect to continuous processing plant rate limiting operations. Note that the optimization routine could optimize batch trajectories directly or only the batch end results within known operational relationships and a separate trajectory calculation could scale 'best-case' trajectories to the currently calculated cycle time and end concentration.

In one embodiment, an optimum would be based on one or more of the objectives above including maximizing production capacity of the entire facility, maximizing processing yield (in cases where due to biomass costs and biofuel pricing yield is driving operations) or a variable costs optimization calculation. The top variable costs of operating a biofuel facility with fermentation are: product value, biomass costs, energy costs and enzyme costs. In most cases energy costs may be related to steam/gas or coal costs and electrical energy costs may be fairly flat (not quite fixed, but mostly fixed) with respect to increasing production.

In one embodiment, economic optimization may be calculated by:

% Biofuel*Fermenter Volume/Batch Time*Biofuel Volumetric cost

Energy Consumption f(1−% Biofuel)*Beer feed rate*Specific

Processing energy cost:

Biomass Mass/Time*Biomass Cost/unit mass

Enzyme Addition/Time*Enzyme Cost/unit added

In one embodiment, the above example equations assume that biofuel concentration may be calculated in volume %, energy consumption function may be developed calculated as a function of beer column feed rate (or ethanol production rate) and amount of water and by-product in the beer column feed (e.g., more water increases processing energy/gallon), biomass usage may be the average mass per unit time (e.g., lb/min,) and enzyme addition may be measured in average enzyme usage during fill (e.g., gpm).

In one embodiment, the extension of the higher level batch controller described above to incorporate fermentation cooling limits through on-line calculations of heat generated or cooling requirements during the targeted biofuel production trajectories. The incorporated cooling can be managed with any of the above controller handles including changes to the biofuel trajectory, changes to the enzyme targets or sugar trajectory constraints, changing fermentation volume or taking advantage of day/night differing cooling capacities in the biofuel trajectories.

In one embodiment, the batch controller described above may be extended to incorporate fermentation cooling limits (generally temperature peaks where fermentation coolers may be saturated) in the controller prediction horizon, which would limit both temperature targets along with enzyme addition rates.

In one embodiment, the details above describing modification of volume to mitigate fermentation limitations with respect to cooling detail may be provided on the issues with temperature control during hot months where cooling water temperatures may be high (detailed above). There may be several other unusual operating strategies available to maximize fermentation performance during cooling limiting periods. Given a representation of interactions between cooling limits and operation in the supervisory (second level) advanced fermentation application, these limits will frequently be as useful as part of the primary batch control, first level advanced batch control, described here. Ultimately limiting constraints would be put on the temperature rather than the cooling water output valve, because this valve may be frequently saturated during any period of peak metabolic batch phase. The principal batch operating issue may be how long the temperature will be out of control, and more importantly how far the temperature may rise above the target.

In one embodiment, if cooling water exchanger duty becomes significant, the first thing a control model can do is project where temperature valves will become saturated and over-cool fermentation before the temperature is saturated to minimize the error from biofuel target across the predictive trajectory. This can be done with a controller on temperature (e.g. model-predictive temperature moving cooling water valve where the temperature will clearly exceed target after the valve is saturated). In this case the temperature controller would naturally over-correct early in the temperature saturation activity, although the prediction horizon may need to include sufficient time to realize that temperature will saturate to enable early corrective action (over four hours for a fifty hour batch with a ten hour fill). Where temperature control is automatic and biofuel concentration control is moving temperature target a second predictive output should be included on temperature valve. This prediction trajectory could be fed back as a nonlinear disturbance variable that will cause biofuel to miss it's target when the valve is projected to be over it's saturation point (e.g. near zero influence up to the saturation value and after it's saturation limit a linear bias equivalent to the expected temperature offset above target). This may cause the temperature target to predictably over-cool before the valve is saturation with the same caveats above and probably an even longer minimum controller horizon.

In one embodiment, another option with the batch controller may be to cool more aggressively during the fill (e.g., there is frequently temperature control on fermentation filling line) and this could in the same way cool more toward the end of the fill when cooling capacity becomes saturated. At it's easiest the cooling water valve may be a constraint variable and once at its limit cooling of the feed could be increased to provide more heat exchanger area and slightly cool off metabolic activity of the active fermentation.

In some parts of the country where day night temperature differences provide additional cooling tower performance at night—it may be possible to manage fermentation temperatures at night since cooling may be more effective to mitigate very high peaks. This would in the best case be tested offline to confirm or understand the costs and benefits of cooling during the early filling periods. In general, large scale fermenters may be filled in a period of between eight to twelve hours (limited by pump capacity and cycle time on other fermenter). The cooling demand and metabolic peak occurs toward the end of the fill and after completing filling for several hours. To mitigate this fermentation could be over-cooled during much of the filling—particularly if the peak will happen mid-day. This is different than much of the optimization work in that manually directed staged temperatures tend to use higher temperatures early in the fermentation (to increase enzyme activity and nutrient availability) and cool later in the fermentation (to extend yeast activity and life). Cooling early in fermentation or staging enzyme addition will reduce temperature peaks, but at some cost by slowing nutrient availability and therefore slowing the availability of feedstock to yeast to convert to biofuel.

The economic answer to this may vary based on plant design and capacity as well as economics and most importantly the current and recent temperature and cooling water limitations during fermentation. It could be calculated in each case using the described nonlinear, dynamic fermentation models including cooling limitations and running either a number of case studies or optimization techniques.

From a general advanced control technology perspective higher level control recognizes operating constraints and lower level control (e.g. as low as possible within controller scope) enforces constraints. This extension would incorporate prediction models based on day/night cooling capacity limits and recent peak metabolic cooling demand to bias a model-based nonlinear batch controller. This model-based information may be used by a predictive control model to manage enzyme and temperature trajectories to avoid high-temperature fermentation limits.

In one embodiment, utilizing the models in the application described in claim number 5 above in conjunction with chiller power consumption and electrical costing equations in an offline fashion to provide specific economic implications of starting fermentation chillers on both the plant economic performance (production and yields within fermentation cooling limits) and electrical power costs. This model use would provide specific plant economic information to bear on the decision to use or not use plant chillers installed to supplement available fermentation cooling. Once in place the same models and system can be used to determine within a month where chillers may be being used, when they should be used and when they should be shut-down.

Frequently the electrical power costs may be calculated not only on the sum of electricity used times energy consumption, but a peak demand multiplier is factored into the electrical energy costs. Thus some plants will pay a monthly adder or multiplier for starting the chillers a single time (increasing plant peak electrical load). In the same way many plants may be in peak or within the summer months limited by cooling capacity and may need to either limit plant capacity or use the supplemental electrical chillers. Without a fermentation model that relates the actual capacity to the increase in capacity and/or yield with and without chillers there is only rules of thumb or rough estimates driving the decision to use or not use this plant equipment (where available). In addition the economics of such decisions will change based on current biofuel, biomass and electrical pricing. These changes make rules of thumb or historic experience doubtful representations to support the best decision.

Chillers come with power curves and should be started at least once every few years to confirm good operation and identify maintenance issues that need to be addressed. For that reason, plants that have chillers installed and consider using them have some data available on electrical energy demand and peak demand during these tests. Where such data is not logged or available costs of chiller operation can be estimated from power curves/design information that is supplied with the chiller equipment by the producer. Electrical costing information can change and be renegotiated, but the information that is the basis of the billing is per contract basis and documented. Where fermentation cooling is the plant bottleneck a case study can be run for starting up the chiller over the next weeks comparing the previous weeks plant rate-limiting constraint (e.g. when is the next capacity limit reached) and the cost of turning on the chiller this month. Based on the electrical billing cycle there may be certain days where this would cover only a few remaining days in the month so off-line calculations may be assumed currently. In addition because the decision to turn on and off the chiller is not made automatically there is not significant advantage of running this calculation on-line.

In one embodiment, chiller usage may be balanced to maximize chilling to the fermenter with the highest cooling demand (e.g. a fermenter operating in exponential growth or production phase) although because of the limited chiller usage (e.g. it is not used throughout the year in most places) there may frequently be complex regulatory control system limits on its operation to protect this equipment (e.g., when in operation, chiller valves may need to be open a minimum of approximately x % to avoid over-pressuring the unit). Within the controller managing temperature/cooling the chiller usage can also be balanced to maximize benefits of the chiller on fermentation performance.

In some embodiments, the fermentation cooling limitations may be part of the fermentation controller problem. In that even chilling will be used to supplement the fermentation cooling to improve temperature control approach to the target biofuel concentration. Generally the chiller valves may be considered disturbance variables that may not be moved by the fermentation controller. In the event that the chiller is turned on—the plant operators would select to automate management of the chillers. This would be particularly useful in the case where chillers may be utilized to avoid chiller trips (which may be bad for equipment longevity and maintenance costs) so the chiller valve positions on each individual fermenter may be used irregularly and operators may be less familiar with their requirements. It is bad to create too much pressure drop or to 'dead head' a chiller where most of the discharge/usage valves may be closed or mostly closed. Secondly the decision to use chilling in cases where there is either too much or too little cooling even with the chillers on-line is best made by the dynamic fermentation controller models.

In one embodiment, a supervisory fermentation application may include management of yeast propagation or inoculation timing and volumes. The objective may be to maximize benefits of yeast concentration and activity at fermenter inoculation.

In some embodiments, the fermentation feed from the prior fermentation vessel may be bypassed to fill a yeast propagation tank (as indicated in the sample fermentation equipment layout above). This tank may be used to start yeast growth, complete the lag phase of yeast acclimation to the fermentation filling environment and to prepare to inoculate the next to be filled fermenter. Timing to fill and inoculate the yeast propagation can be critical to assuring that the yeast is fully active and has sufficient time to build concentrations at targeted inoculation concentrations to start the fermenter. While fairly straight-forward on a conservatively operated fixed cycle-time batch operation—issues from either changing cycle times (filling and dropping fermentations faster or slower than custom based on performance objectives) or distracting plant operational issues, timing can be non-ideal. As the solutions above calculate targeted cycle times, fermentation feed biomass solids concentrations and continuous plant processing rates, they can be configured to either alert an operator through control system alarms or automatically start yeast propagation activities and perform similar functions when it is the best time to inoculate the fermenter (e.g. open valves to send yeast propagation with active yeasts to the filling fermenter). Alternatively, where active yeast slurry is directly feed to a fermenter or a fermenter is directly and manually added dried yeast blocks such an application would trigger (through direct regulatory control or operator alarms) when and how much innoculum to add.

While actively managing the yeast activity and concentration through these process options (e.g., plant equipment configuration), the models of biofuel production may have improved information on yeast concentration and activity. This improves not only the yeast inoculation and therefore the fermenter performance and consistency, but would improve the fermenter performance models through earlier and better information on items critical to this performance.

The benefit of this management of yeast propagation may be a consistently good start to each fermentation even in the event of other plant disruptions or activity (although frequently manual operations will be required).

In one embodiment, inferred property models of one or more of the fermentation results described above may be developed and deployed on-line. Empirical, fundamental or hybrid (empirical and fundamental) modeling techniques may be applied to predict batch ethanol, sugar, dextrin or yeast concentration and/or yeast activity as each batch progresses to provide real-time feedback to the batch controllers described above or simply as an operator advisory/monitoring measurement.

Models may be developed as functions of batch starting/ filling, inoculation and processing conditions on one or more of these measured properties. This may include functions of temperature, biomass concentration (or mass), water content (e.g., contaminant levels, recycle quantities or sources), pH, enzyme addition, yeast conditions, cooling requirements and batch progress (e.g., batch-time, current ethanol concentration or other measured indicators). Such a system may be configured to execute on-line and calculate information for direct communication through various control systems and trending packages. An inferred property model is in general configured to enable on-line biasing when new laboratory or on-line sampling information becomes available. In this way general trends in fermentation performance from undetected changes (e.g., biomass quality, yeast quality, input measurement drift) can be gradually corrected.

In some embodiments, a dynamic inferred property may be preferred. For example, the better the inferred property model relationship to the process relationships that may be measured the higher the trust factor in the model and the further fermentation performance can be performed. In the event that and online analyzer can provide real-time feedback to the described control model system a separate inferred property model may or may not be required. In most cases it may be useful to have a separate inferred property model because the control model represents in most case the nonlinear gain and dynamic relationships although does not use state and indirect measured properties that support the inferred property model. (e.g., cooling exchanger duty, fermentation DE: dextrose equivalent as measured . . . ). These can be used to improve the accuracy of the inferred property model, but can misdirect the control model. In any case a dynamic inferred property model improves accuracy because if temperature changes may be in process of being made only part of the response has occurred and to synchronize the measurement at any point (e.g. model verification and biasing) a better model provides a better match and enables a more aggressive biasing and in most cases less significant biasing.

In one embodiment, the inferred property model may run online and may provide real-time feedback for the controller in the event that an online analyzer or measurement may not be available, but may be desired for feedback to the controller.

Thus, various embodiments of the above model predictive control systems and methods may be used to manage a fermentation process in a biofuel production process.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications. Note the section headings used herein are for organizational purposes only and are not meant to limit the description provided herein or the claims attached hereto.

We claim:

1. A method for managing a batch fermentation process in a biofuel production process, comprising:
   providing a nonlinear control model, comprising a nonlinear predictive model of a batch fermentation process of a biofuel production process, wherein the nonlinear predictive model is a function of a volumetric change in a fermentation tank, temperature, and enzyme concentration;
   providing an optimal batch temperature trajectory;
   executing the nonlinear control model in accordance with the optimal batch temperature trajectory, thereby generating model output comprising target values for a plurality of manipulated variables for the batch fermentation process, wherein the target values comprise a target enzyme addition staging profile during filling of the fermentation tank; and
   controlling an enzyme addition rate during filling of the fermentation tank in accordance with the target enzyme addition staging profile.

2. The method of claim 1, wherein the nonlinear control model further comprises a shrinking temporal control horizon during the batch fermentation process;
   wherein the method further comprises providing an end-of batch biofuel concentration objective to the nonlinear predictive model; and
   wherein providing the optimal batch temperature trajectory comprises causing an optimizer to execute the nonlinear predictive model, thereby determining the optimal batch temperature trajectory over the shrinking temporal control horizon in accordance with the end-of-batch biofuel concentration objective.

3. The method of claim 2, further comprising:
   receiving a constraint on sugar concentration over the batch fermentation process, or a constraint on end-of-batch sugar concentration.

4. The method of claim 3, wherein the optimal batch temperature trajectory over the shrinking temporal control horizon is determined subject to the constraint.

5. The method of claim 3, wherein the target values for the plurality of manipulated variables are determined subject to the constraint.

6. The method of claim 1, further comprising:
   repeating said executing the nonlinear control model, and said controlling, in an iterative manner.

7. The method of claim 6, wherein said repeating said executing the nonlinear control model further comprises generating target values comprising a fermentation temperature staging profile for the fermentation batch.

8. The method of claim 1, wherein the nonlinear predictive model is further a function of yeast concentration, yeast addition, yeast activity, biomass concentration, batch progress, or pH.

9. A computer-accessible memory medium that stores program instructions for managing a batch fermentation process in a biofuel production process, wherein the memory medium stores:
   a nonlinear control model, comprising a nonlinear predictive model of a batch fermentation process of a biofuel production process, wherein the nonlinear predictive model is a function of a volumetric change in a fermentation tank temperature, and enzyme concentration;
   program instructions executable to:
      provide an optimal batch temperature trajectory;
      execute the nonlinear control model in accordance with the optimal batch temperature trajectory, thereby generating model output comprising target values for a plurality of manipulated variables for the batch fermentation process, wherein the target values comprise a target enzyme addition staging profile during filling of the fermentation tank; and
      control an enzyme addition rate during filling of the fermentation tank in accordance with the target enzyme addition staging profile.

10. The memory medium of claim 9, wherein the nonlinear control model further comprises a shrinking temporal control horizon during the batch fermentation process;
   wherein the program instructions are further executable to provide an end-of batch biofuel concentration objective to the nonlinear predictive model; and
   wherein the program instructions that are executable to provide the optimal batch temperature trajectory comprise program instructions that cause an optimizer to execute the nonlinear predictive model, thereby determining the optimal batch temperature trajectory over the shrinking temporal control horizon in accordance with the end-of-batch biofuel concentration objective.

11. The memory medium of claim 10, wherein the program instructions are further executable to receive a constraint on sugar concentration over the batch fermentation process, or a constraint on end-of-batch sugar concentration.

12. The memory medium of claim 11, wherein the optimal batch temperature trajectory over the shrinking temporal control horizon is determined subject to the constraint.

13. The memory medium of claim 11, wherein the target values for the plurality of manipulated variables are determined subject to the constraint.

14. The memory medium of claim 9, wherein the program instructions are further executable to repeat said executing the nonlinear control model, and said controlling, in an iterative manner.

15. The memory medium of claim 14, wherein said repeating said executing the nonlinear control model further comprises generating target values comprising a fermentation temperature staging profile for the fermentation batch.

16. The memory medium of claim 9, wherein the nonlinear predictive model is further a function of yeast concentration, yeast addition, yeast activity, biomass concentration, batch progress, or pH.

17. A system for managing a batch fermentation process in a biofuel production process, comprising:
a fermenter;
a nonlinear control model, comprising a nonlinear predictive model of a batch fermentation process of a biofuel production process, wherein the nonlinear predictive model is a function of a volumetric change in a fermentation tank temperature, and enzyme concentration; and
a control system operatively coupled to the nonlinear control model and the fermenter, wherein the control system is operable to:
provide an optimal batch temperature trajectory;
execute the nonlinear control model in accordance with the optimal batch temperature trajectory, thereby generating model output comprising target values for a plurality of manipulated variables for the batch fermentation process, wherein the target values comprise a target enzyme addition staging profile during filling of the fermentation tank; and
control an enzyme addition rate during filling of the fermentation tank in accordance with the target enzyme addition staging profile.

18. The system of claim 17, wherein the nonlinear control model further comprises a shrinking temporal control horizon during the batch fermentation process;
wherein the control system is further operable to provide an end-of batch biofuel concentration objective to the nonlinear predictive model; and
wherein providing the optimal batch temperature trajectory comprises causing an optimizer to execute the nonlinear predictive model, thereby determining the optimal batch temperature trajectory over the shrinking temporal control horizon in accordance with the end-of-batch biofuel concentration objective.

19. The system of claim 18, wherein the control system is further operable to receive a constraint on sugar concentration over the batch fermentation process, or a constraint on end-of-batch sugar concentration.

20. The system of claim 19, wherein the optimal batch temperature trajectory over the shrinking temporal control horizon is determined subject to the constraint.

21. The method of claim 19, wherein the target values for the plurality of manipulated variables are determined subject to the constraint.

22. The system of claim 17, wherein the control system is further operable to repeat said executing the nonlinear control model, and said controlling, in an iterative manner.

23. The system of claim 22, wherein said repeating said executing the nonlinear control model further comprises generating target values comprising a fermentation temperature staging profile for the fermentation batch.

24. The system of claim 17, wherein the nonlinear predictive model is further a function of yeast concentration, yeast addition, yeast activity, biomass concentration, batch progress, or pH.

25. The system of claim 17, wherein the control system is distributed over a plurality of computers.

* * * * *